United States Patent
Denvir et al.

(10) Patent No.: US 9,707,520 B2
(45) Date of Patent: *Jul. 18, 2017

(54) COMPOSITION, SYSTEM, AND METHOD FOR TREATING WATER SYSTEMS

(71) Applicant: NCH Corporation, Irving, TX (US)

(72) Inventors: Adrian Denvir, Richardson, TX (US); James Gregory Edford, Richland Hills, TX (US); Angela L Delegard, Denton, TX (US); Scott M Boyette, Irving, TX (US)

(73) Assignee: NCH Corporation, Irving, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/237,052

(22) Filed: Aug. 15, 2016

(65) Prior Publication Data

US 2016/0354727 A1    Dec. 8, 2016

Related U.S. Application Data

(63) Continuation-in-part of application No. 13/745,211, filed on Jan. 18, 2013, now Pat. No. 9,452,457.
(Continued)

(51) Int. Cl.
  *B08B 7/04* (2006.01)
  *B01D 65/08* (2006.01)
  (Continued)

(52) U.S. Cl.
  CPC ............ *B01D 65/08* (2013.01); *A01N 37/36* (2013.01); *A01N 59/00* (2013.01); *B01D 61/002* (2013.01);
  (Continued)

(58) Field of Classification Search
  CPC .................................................. B08B 3/04
  See application file for complete search history.

(56) References Cited

U.S. PATENT DOCUMENTS

| | | |
|---|---|---|
| 1,674,281 A | 6/1928 | Fleming |
| 3,106,541 A | 10/1963 | Lipowski et al. |
| | (Continued) | |

FOREIGN PATENT DOCUMENTS

| | | |
|---|---|---|
| DE | 19859774 | 6/2000 |
| WO | WO2005021445 | 3/2005 |
| | (Continued) | |

OTHER PUBLICATIONS

Marigot Ltd. "GRAS Notification with respect to Phymatolithon calcareum and Lithothamnium corallioides" Jul. 1999.
(Continued)

*Primary Examiner* — Bibi Carrillo
(74) *Attorney, Agent, or Firm* — Ross Barnes LLP; Monty L. Ross; Robin L. Barnes

(57) ABSTRACT

A composition for treating a water system or membrane fluid system, such as a reverse osmosis system, to remove scale, microorganisms and biofilm, and corrosion by-products. The composition comprises chelating agents and a surfactant. The composition may be a solid dissolved by water or solvent in the system being treated or may be a pre-mixed foam or aerosol. A method for using such a treatment composition comprises contacting the treatment composition with substantially all parts of the water system and draining the treatment composition from the system before resuming normal operations. For certain systems, the method also comprises draining some existing water in the water system to remove prior treatment compositions and filling or rinsing the system with fresh water prior to adding the treatment composition.

14 Claims, 15 Drawing Sheets

Related U.S. Application Data

(60) Provisional application No. 61/587,966, filed on Jan. 18, 2012.

(51) Int. Cl.

| | | |
|---|---|---|
| *A01N 59/00* | (2006.01) | |
| *C11D 3/20* | (2006.01) | |
| *C11D 3/48* | (2006.01) | |
| *C02F 1/68* | (2006.01) | |
| *B01D 61/00* | (2006.01) | |
| *B01D 61/02* | (2006.01) | |
| *B01D 61/14* | (2006.01) | |
| *A01N 37/36* | (2006.01) | |
| *B08B 9/08* | (2006.01) | |
| *C02F 1/50* | (2006.01) | |
| C02F 1/44 | (2006.01) | |
| C11D 1/38 | (2006.01) | |
| C11D 3/33 | (2006.01) | |
| B08B 3/04 | (2006.01) | |
| B08B 9/00 | (2006.01) | |
| C02F 1/00 | (2006.01) | |
| C02F 1/76 | (2006.01) | |
| C02F 101/30 | (2006.01) | |
| C02F 103/02 | (2006.01) | |

(52) U.S. Cl.
CPC ......... *B01D 61/025* (2013.01); *B01D 61/027* (2013.01); *B01D 61/145* (2013.01); *B01D 61/147* (2013.01); *B08B 9/0856* (2013.01); *C02F 1/50* (2013.01); *C02F 1/68* (2013.01); *C02F 1/683* (2013.01); *C11D 3/2086* (2013.01); *C11D 3/48* (2013.01); *B08B 3/04* (2013.01); *B08B 9/00* (2013.01); *C02F 1/001* (2013.01); *C02F 1/008* (2013.01); *C02F 1/441* (2013.01); *C02F 1/442* (2013.01); *C02F 1/444* (2013.01); *C02F 1/445* (2013.01); *C02F 1/685* (2013.01); *C02F 1/687* (2013.01); *C02F 1/76* (2013.01); *C02F 1/766* (2013.01); *C02F 2101/30* (2013.01); *C02F 2103/023* (2013.01); *C02F 2303/02* (2013.01); *C02F 2303/04* (2013.01); *C02F 2303/08* (2013.01); *C02F 2303/20* (2013.01); *C02F 2303/22* (2013.01); *C02F 2305/04* (2013.01); *C02F 2305/14* (2013.01); *C02F 2307/08* (2013.01); *C11D 1/38* (2013.01); *C11D 3/33* (2013.01)

(56) References Cited

U.S. PATENT DOCUMENTS

| | | | |
|---|---|---|---|
| 3,123,554 | A | 3/1964 | Murray |
| 3,173,864 | A | 3/1965 | Freedman |
| 3,410,649 | A | 11/1968 | Sellet |
| 3,428,557 | A | 2/1969 | Rivers |
| 3,503,890 | A | 3/1970 | Davisson et al. |
| 3,582,461 | A | 6/1971 | Lipowski et al. |
| 4,005,009 | A | 1/1977 | Kinoshita et al. |
| 4,306,967 | A | 12/1981 | Trautwein |
| 4,383,077 | A | 5/1983 | Bankert |
| 4,830,761 | A | 5/1989 | Leach et al. |
| 4,931,187 | A | 6/1990 | Derham et al. |
| 5,057,229 | A | 10/1991 | Schulenburg |
| 5,253,759 | A | 10/1993 | Gouge et al. |
| 5,294,916 | A | 3/1994 | Bolton et al. |
| 5,322,856 | A | 6/1994 | Martin |
| 5,576,481 | A | 11/1996 | Beardwood |
| 5,874,026 | A | 2/1999 | Pilsits, Jr. et al. |
| 6,040,406 | A | 3/2000 | Carrier et al. |
| 6,063,290 | A | 5/2000 | Failon et al. |
| 6,149,821 | A | 11/2000 | Rounds et al. |
| 6,149,822 | A | 11/2000 | Fabri et al. |
| 6,183,649 | B1 | 2/2001 | Fontana |
| 6,346,275 | B1 | 2/2002 | Auchincloss |
| 6,498,137 | B1 | 12/2002 | Schalitz et al. |
| 6,701,940 | B2 | 3/2004 | Tsibouklis et al. |
| 6,746,609 | B2 | 6/2004 | Stander |
| 6,797,197 | B2 | 9/2004 | Steimel et al. |
| 6,840,251 | B2 | 1/2005 | Gill et al. |
| 7,141,174 | B2 | 11/2006 | Steimel et al. |
| 7,537,705 | B2 | 5/2009 | Mizuno et al. |
| 7,632,412 | B2 | 12/2009 | Johnson et al. |
| 7,959,943 | B2 | 6/2011 | Hissong et al. |
| 7,976,873 | B2 | 7/2011 | Myntti et al. |
| 7,993,675 | B2 | 8/2011 | Oliver et al. |
| 8,668,779 | B2 * | 3/2014 | Cooper ............ A61L 2/16 134/22.1 |
| 2002/0185419 | A1 | 12/2002 | Chandler |
| 2003/0094406 | A1 | 5/2003 | Smith |
| 2003/0105072 | A1 | 6/2003 | Degenhardt et al. |
| 2003/0108705 | A1 | 6/2003 | Duffield et al. |
| 2003/0200997 | A1 | 10/2003 | Gill et al. |
| 2004/0007255 | A1 | 1/2004 | Labib et al. |
| 2005/0013878 | A1 | 1/2005 | Mingzhong et al. |
| 2005/0040363 | A1 | 2/2005 | Gray |
| 2007/0264296 | A1 | 11/2007 | Myntti |
| 2008/0017337 | A1 | 1/2008 | Duggirala et al. |
| 2008/0035580 | A1 | 2/2008 | de Rijk |
| 2008/0169239 | A1 | 7/2008 | Sparks et al. |
| 2009/0258086 | A1 | 10/2009 | Myntti |
| 2010/0086576 | A1 | 4/2010 | Myntti |
| 2010/0261631 | A1 | 10/2010 | Isobe et al. |
| 2011/0008220 | A1 | 1/2011 | Fleming et al. |
| 2011/0081713 | A1 | 4/2011 | Fleming et al. |
| 2011/0217761 | A1 | 9/2011 | Hilgren et al. |
| 2011/0293481 | A1 | 12/2011 | Eanes et al. |
| 2012/0067793 | A1 | 3/2012 | Ferrari et al. |
| 2012/0258156 | A1 | 10/2012 | Rumberger et al. |
| 2013/0099158 | A1 | 4/2013 | Moore et al. |
| 2013/0239991 | A1 | 9/2013 | Denvir et al. |
| 2014/0263075 | A1 | 9/2014 | Madsen et al. |
| 2015/0125544 | A1 | 5/2015 | Henderson et al. |
| 2015/0126425 | A1 | 5/2015 | Henderson et al. |
| 2016/0304367 | A1 * | 10/2016 | Gillespie ............ A01N 25/12 |

FOREIGN PATENT DOCUMENTS

| | | |
|---|---|---|
| WO | WO2005051850 | 6/2005 |
| WO | WO2013090569 | 6/2013 |
| WO | WO2013163146 | 10/2013 |
| WO | WO2014155147 | 10/2014 |

OTHER PUBLICATIONS

M.A. Patrauchan et al., Calcium influences cellular and extracellular product formation during biofilm-associated growth of a marine *Pseudoalteromonas* sp., Journal 2005, 13 pg.

* cited by examiner

COMPOSITION, SYSTEM, AND METHOD FOR TREATING WATER SYSTEMS

CROSS-REFERENCE TO RELATED APPLICATION

This application is a continuation-in-part of U.S. application Ser. No. 13/745,211 filed on Jan. 18, 2013, now U.S. Pat. No. 9,452,457, which claims the benefit of U.S. provisional patent application No. 61/587,966 filed Jan. 18, 2012.

BACKGROUND OF THE INVENTION

1. Field of the Invention

This invention relates to a treatment composition, system, and method for treating water systems for scale, biofilm and microbial growth, and corrosion. This invention is particularly useful in anthropogenic cooling and chilled water applications, such as cooling towers, and in drain systems, such as floor drains, hospital drains and waterless urinals, and for treating reverse osmosis membrane systems.

2. Description of Related Art

Anthropogenic water systems are critical components commonly found in most of the world's energy producing facilities, industrial and manufacturing plants, hospitals, and other institutional complexes and buildings. These systems consume around 700 billion gallons of water annually with a cost of $1.8 billion in sewage handling costs alone. All of these anthropogenic water systems require some form of treatment, either chemical or non-chemical, to control the build-up of scale, biofilm and other corrosion by-products on the important heat transfer surfaces that are necessary for efficient system operation.

For water systems involving heat exchange, such as cooling towers, effective treatment to remove these contaminants and to prolong the amount of time before the systems are re-contaminated can safe significant amounts of money. An effective and thorough treatment may save costs for labor and treatment chemicals by reducing the frequency of periodic treatments or reducing the amount of chemicals needed for routine maintenance and/or periodic treatments. Such a treatment may also save on energy costs through the operation of clean heat exchange surfaces. Fouling of heat exchange surfaces costs U.S. industry hundreds of millions of dollars every year and is directly related to an increase in energy consumption of almost 3 quadrillion Btus (quads) annually.

To maximize the water usage and minimize waste, many of these systems employ a series of chemical treatments that protect the system against scaling, biofilm formation, and corrosion. For example the Chem-Aqua 15000 MTP product is one of the most common cooling tower chemical treatments, containing 2-phosphonobutane-1,2,4-tricarboxylic acid, and a series of high performance polymers to prevent calcium carbonate scale formation, azoles to inhibit copper corrosion and small amounts of molybdate for trace analysis. Chemical treatments such as the Chem-Aqua 15000 MTP product may be used with a number of non-oxidizing biocides including Bacticide 45 which is a 45% gluteraldehyde solution, Coolicide which is a 15% poly-quaternary ammonium solution, or a 1.5% Isothiazolin solution. In the larger industrial cooling tower systems and the cooling towers for coal and nuclear facilities it is more common to use sodium hypochlorite, 40% sodium bromide, or 11% bromine chloride liquid as the disinfectants.

These chemical treatments allow the water to be reused and recycled a number of times before it becomes necessary to discharge the water and replace it with fresh water. Increasing the duration for which the water may be circulated significantly reduces the amount of water that is discharged to the sewage system and minimizes the amount of make-up water that is needed to replace the bleed off. The chemical treatments also maintain the efficiency of the cooling tower and heat exchanger system. Many prior art treatment compositions and methods involve the use of liquid chemicals, typically shipped in large drums, which may make shipping and handling of the chemical compositions more difficult and expensive. Additionally, many prior art treatment compositions and methods may damage the components of the water system being treated as the chemicals used are highly corrosive. There is also an environmental down side to the treatments. It is estimated that there are 536 billion pounds of water treatment chemicals discharged as a result of cooling tower treatments every year, which may impact a variety of species living in or near areas and water-ways receiving the discharge. Therefore it is desirable to use treatment chemicals that are considered less toxic. For example, citric acid and sodium citrate, which are both approved food additives, have been used in treatment compositions.

Many prior art treatment compositions and methods are also effective at removing biofilms or require the use of strongly acidic, oxidizing, and toxic biocides for removal. Biofilms contain mixed communities of bacteria including various species embedded in an exopolymer or "slime layer". As bacteria begin to attach to a surface, they secrete polymers, such as polysaccharides and glycoproteins called fibronectin. These allow the bacteria to adhere to a surface and form the conditioning layer of the biofilm. Once a confluent surface of sessile cells has formed, any other bacteria that contact this layer will be captured. Thus bound in this way, these bacterial cells begin to produce anchoring organelles and other compounds, allowing a secondary layer to form on top of the conditioning layer. As cells continue to attach and accumulate, underlying layers continue to reproduce and create a dense bacterial cluster. As these biofilm layers form they also accumulate other inorganic and organic debris that grow within the pipe restricting flow and causing blockages.

Similar issues, particularly with biofilms, are also encountered in drainage systems, such as hospital drains, industrial wastewater drains, and waterless urinals. During normal use, drains and drainage systems transport liquids such as water, urine, or processing fluids to treatment or discharge facilities. Even though some of these liquids are sterile when then enter the drain systems, it is virtually impossible to keep all fluids sterile when they enter the outside environment. As they flow through the drainage system they accumulate naturally occurring micro flora and other heterotrophic microorganisms that, over time, result in the formation of biofilms along the surfaces of the walls of the pipes. In hospitals, especially dialysis centers, this could present a direct risk of infection to patients. Biofilms may also grow rapidly and result in clogged drains and piping in drainage systems.

Products and services for the cleaning and remediation of drains and drainage systems worldwide is estimated to exceed $2 billion annually, most of which is driven by labor costs that consume $0.87 for every dollar spent. As with the chemicals used to clean cooling tower and similar industrial water systems, the prior art drain remediation and cleaning technologies use aggressive chemicals, including concentrated acidic or basic compounds. These compounds need special handling and have to be stored on site or require specialty power cleaners such as water jets or drum and sectional machines that require experienced operators. They also typically involve added costs for protective gear for operators handling the chemicals and added training cots.

Many of the chemical drain cleaning products are sold in solid or liquid forms and are classified as alkaline drain openers, acid drain openers, or enzymatic drain cleaners. Alkaline drain openers come as either a solid or liquid and typically contain sodium or potassium hydroxide as well as sodium hypochlorite. In some cases the alkaline drain openers are sold as two part mixtures that will form a foam when mixed together in the drain. Alkaline drain openers can dissolve proteins and fats within the drain through an alkaline hydrolysis of the amide or ester. Acid drain openers usually contain a strong acid such as sulfuric acid that dissolves fats and proteins via an acid hydrolysis mechanism. They also have dehydrating properties that help them dissolve paper. Unlike the alkaline drain openers, most of these acid cleaners must be applied by a licensed operator. Enzymatic drain cleaners use bacterial cultures and concentrated enzymes that react with organic residues on the walls of the pipes, dissolving it to keep the drain flowing. These drain cleaners are intended to be used as a general maintenance treatments and not to remove clogs or blockages that have already formed. Mechanical drain cleaners are also known in the prior art and involve a number of mechanical and physical techniques to unclog and clean drain systems, which may be used alone or in combination with chemical cleaners. These mechanical cleaners include auger systems, air burst systems, plumber snakes, and water jet systems. These mechanical systems are advantageous because they do not have the hazards associated with the storage and use of harsh chemicals and they are relatively inexpensive and readily available for rent in most hardware stores. However, the disadvantage is that the mechanical removal of clogs and other biological deposits with these methods can be expelled into the environment putting the operator and other people in the vicinity at risk of exposure to biological pathogens. This is of particular concern in hospitals and dialysis centers where immunocompromised patients are being treated.

Biofilm growth or biofouling is also a major issue in reverse osmosis systems, such as desalination plants. Reverse osmosis is a type of water treatment process that removes inorganics and organics from solution. These systems use a semi-permeable membrane to allow water to flow through the membrane by applying high pressure to overcome osmotic pressure. Reverse osmosis systems vary in size depending on application, and can treat multiple types of water such as brackish and sea water. Reverse osmosis systems also include pre-treatments (chemical feed, coagulation/flocculation/sedimentation, sand filtration, microfiltration (MF), and ultrafiltration (UF)) and post-treatments (UV disinfection). Biofouling in a reverse osmosis system increases energy consumption in order to maintain the system's feed pressure, reduces permeate flux, and increases the amount of chemical feed needed to clean the membrane. With increased chemical feed, the lifespan of the membrane will decrease due to the degradation of the membrane, which allows more solids to pass through the membrane which would require more post-treatment of the permeate flux. Prior art biological control products, such as alkaline cleaners or non-oxidizers, have been used to reduce or prevent the formation of biofilm. However, these products are either too corrosive and could destroy the integrity of the membrane, or highly toxic. Depending on their size, membranes cost from around $258.00 to $767.00, making it important to prolong the life of the membrane as much as possible. With prior art treatments, the average lifespan of a reverse osmosis spiral-wound membrane is 3 years

SUMMARY OF THE INVENTION

This invention relates to a chemical treatment composition, system and method for treating water systems, such as anthropogenic cooling and chilled water systems and drain systems, including dialysis and x-ray drains, urinals in port-o-potties, p-trap, and waterless urinals. Generally, these water systems are either "flowing" (or circulating or otherwise involving moving fluids) or "non-flowing" systems (or non-circulating systems) based on whether water is flowing through the system at the time of treatment. For example, a cooling tower would typically be a flowing system because water circulates through the system during treatment, whereas a drain would typically be a non-flowing system because water is not running through the drain during treatment. There are preferred embodiments for both types of water systems described herein; however, with modifications understood by those of ordinary skill in the art a water system may be switched from a flowing system to a non-flowing system, as desired, and a preferred embodiment for one type of system may be adapted for application to a water system that is typically considered to be the other type of system (for example, application of a non-flowing embodiment to a cooling tower) within the scope of the invention.

According to a preferred embodiment for a flowing water system or a reverse osmosis system, the treatment system comprises a side stream and a treatment product feeder containing a solid treatment product, preferably a product according to the treatment composition of the invention. A portion of the water from the system being treated is diverted to the side stream, where it contacts and dissolves the solid treatment product in the product feeder. The side stream, with the dissolved treatment product, is then reintroduced into the water system for further dilution and circulation throughout the system. The water containing the dissolved treatment product is then circulated throughout the water system for an effective period of time. The treatment system preferably includes a corrosion rack/corrosion monitor and a conductivity meter to monitor the effectiveness of the treatment product and the level of corrosion caused by the treatment product on the components of the water system being treated. According to another preferred embodiment, the treatment system comprises an in-line filtration mechanism to filter out biofilm agglomerates dislodged by the treatment composition. When treating a reverse osmosis system, it is preferred to treat the entire system by allowing the treatment composition to circulate through and contact all components of the system, but a secondary treatment system loop to treat only the membrane may also be used.

A treatment composition according to one preferred embodiment of the invention, applicable to both flowing and non-flowing water systems, comprises chemical chelating agents (organic or inorganic acids and their corresponding neutral salts for metal ion sequestration from biofilm, hard scale, and bulk water) and a surfactant. Citric acid and sodium citrate are preferred chelating agents and tetradecyltrimethyl ammonium bromide is a preferred surfactant. The composition may comprise citric acid and sodium bicarbonate, which will react to generate sodium citrate. When added to the water of the flowing water system being treated or with a given volume of water in a preferably pre-mixed, ready-to-use liquid or foaming formulation for treatment of non-flowing water systems, these reagents are preferably in concentrations of at least 0.001 M neutral salt, 0.0005 M acid salt, and 0.00015 M surfactant, but not greater than 0.01 M neutral salt, 0.005 M acid salt, and 0.0015 M surfactant. One or more corrosion inhibitors, particularly copper inhibitors such as tolyltriazole ("TTA"), are also preferably used with the reagents in the treatment composition in concentrations according to label specifications, typically between 2 ppm-17 ppm. A secondary biocide and/or anti-foaming agents are also preferably added to or used with the treatment composition for controlling microorganisms and water parasites and foaming.

A treatment composition according to one preferred embodiment of the invention, particularly applicable to treating membranes and other components in a fluid system, such as reverse osmosis, nanofiltration, ultrafiltration, microfiltration, forward osmosis, and conventional particle filtration systems, comprises chemical chelating agents (organic or inorganic acids and their corresponding neutral salts for metal ion sequestration from biofilm, hard scale, and bulk water) and a surfactant. Citric acid and sodium citrate are preferred chelating agents and tetradecyltrimethyl ammonium bromide is a preferred surfactant. The composition may comprise citric acid and sodium bicarbonate, which will react to generate sodium citrate. When added to the water of the reverse osmosis or other membrane system being treated, these reagents are preferably in concentrations of at least 0.001 M neutral salt, 0.0005 M acid salt, 0.00015 M surfactant, (the ratio of neutral salts and acid salts can be generated by reacting sodium bicarbonate with citric acid), but not greater than 0.01 M neutral salt, 0.005 M acid salt, 0.0015 M surfactant. One or more corrosion inhibitors, particularly copper inhibitors such as tolyltriazole ("TTA"), are also preferably used with the reagents in the treatment composition in concentrations according to label specifications, typically between 2 ppm-17 ppm. A secondary biocide and/or anti-foaming agents are also preferably added to or used with the treatment composition for controlling microorganisms and water parasites and foaming.

In order to achieve the minimum concentrations of treatment compositions described above to treat a small volume water system, it would be necessary to ship large volumes of liquid-based chemicals even when the volume of the water system being treated is relatively small. Shipping and handling such large volumes of liquid chemicals is costly and can be hazardous to personnel involved in the cleaning process. It is possible to produce and ship smaller volumes of concentrated liquid chemicals to use as the treatment composition. Using certain chelating agents and certain surfactants, such as tetradecyltrimethyl ammonium bromide and didecyldimethyl ammonium chloride, a 70× concentrated liquid formula is possible. However, use of a concentrated liquid formula limits the type of surfactant that can be used, because certain surfactants, such as SugaQuats, will precipitate from solution rendering the mixture inactive. Additionally, shipping and handling concentrated liquid treatment compositions can still be more costly and hazardous that if the treatment composition were in a solid form. Preferably, at least one component of the treatment compositions is in a solid form that uses the water in the system being treated to dissolve and dilute the composition.

Drain systems typically require smaller amounts of treatment chemicals. Although handling such chemicals may still be hazardous, the issues related to shipping large quantities of the chemicals are not typically encountered. Additionally, unlike other circulating water systems, it may be more difficult for the treatment composition to contact all contaminated surfaces in a drainage system. A spray, flooded aerosolized or foaming formulation for the treatment composition is preferably used for drainage systems to aid in having the treatment reach all surfaces of the drain.

A method for treating water systems according to a preferred embodiment of the invention for a flowing water system comprises the steps of (1) bleeding or draining at least some of water from the water system and re-filling, as necessary, to remove some of the existing water and any previous water treatment compositions that may react with or otherwise interfere with the treatment composition; (2) determining the total volume of water in the system and re-filling the system with water as needed; (3) adding a treatment composition so that the final concentrations of active reagents in the water system are greater than 0.001 M neutral salt, 0.0005 M acid salt, 0.00015 M surfactant; (4) optionally adding corrosion inhibitors (typically 2 ppm minimum), anti-foaming agents, and/or a secondary biocide, as desired; (5) circulating the water with the treatment composition throughout the system for a sufficient time; (6) periodically testing the system for corrosion products to monitor the corrosive effects of the treatment composition on the water system; (7) filtering the water to remove dislodged solids and biofilm agglomerates and monitoring the filter for necessary replacement; and (8) bleeding or draining the water containing the treatment composition from the water system after sufficient treatment time and removing any remaining solids in the sump or other water reservoir or low flow areas of the system, then refilling with fresh water.

A method for treating a membrane system, such as reverse osmosis, nanofiltration, ultrafiltration, microfiltration, forward osmosis, and conventional particle filtration systems according to a preferred embodiment of the invention comprises the steps of (1) optionally draining at least some water (or other fluid) from the membrane system and re-filling, as necessary, to remove some of the existing water and any previous water treatment compositions that may react with or otherwise interfere with the treatment composition and re-filling the system with water (or other fluid) as needed; (2) determining the total volume of water (or other fluid) in the system; (3) adding a treatment composition so that the final concentrations of active reagents in the water (or other fluid) system at least 0.001 M neutral salt, 0.0005 M acid salt, and 0.00015 M surfactant (the ratio of neutral salts and acid salts may be generated by reacting sodium bicarbonate with citric acid) (4) optionally adding corrosion inhibitors (typically 2 ppm minimum), anti-foaming agents, and/or a secondary biocide, as desired; (5) circulating the water with the treatment composition throughout the system (or a portion of the system, preferably at least the membrane) for a sufficient time; (6) periodically testing the system for corrosion products to monitor the corrosive effects of the treatment composition on the water system; (7) filtering the water to remove dislodged solids and biofilm agglomerates and monitoring the filter for necessary replacement; (8) bleeding or draining the water containing the treatment composition from the reverse osmosis system after sufficient treatment time; and (9) rinsing the membrane system (or portion thereof that was treated) and then refilling with fresh water (or other fluid) and resuming normal operations as desired.

A method for treating water systems according to a preferred embodiment of the invention for a periodic or non-circulating flowing water system comprises the steps of: (1) optionally flushing the water system with fresh water; (2) optionally preparing a liquid, aerosol, or foaming treatment composition at the treatment site so that the final concentrations of active reagents in the water system are greater than 0.001 M neutral salt, 0.0005 M acid salt, 0.00015 M surfactant based on the volume of water used to prepare the treatment (alternatively, the treatment composition may be shipped as a pre-mixed or ready-to-use formulation); (3) applying the treatment composition to the water system by pouring, spraying, or foaming; (4) optionally adding corrosion inhibitors (typically 2 ppm minimum) and/or a secondary biocide, as desired; (5) re-applying the treatment composition to the water system as needed so that the total contact time of the treatment composition with substantially all contaminated surfaces in the water system is sufficient; (6) optionally testing the system periodically for corrosion products to monitor the corrosive effects of the treatment composition on the water system; and (7) optionally flushing the water system with fresh water.

As used herein, "fresh" water includes any source of water that is supplied to the water system from an available water source, such as a municipal water supply, a well, river, pond, lake, sea or ocean, or water recycled from another industrial process. Most typically, this water is from a municipal water supply. These methods result in a thorough cleaning of the water system, after which other, conventional water treatment regimens may be resumed and these methods utilized for periodic maintenance. Most preferably, the concentrations of active reagents of the treatment composition used with these preferred methods (when mixed with the water of the system for a flowing water system or when mixed with a given volume of water from an external source for a non-flowing water system) are 0.005 M neutral salt, 0.003 M acid salt, 0.00075 M surfactant for use with flowing water systems, such as cooling towers, and are 0.005 M neutral salt, 0.003 M acid salt, and 0.00075 M surfactant, for use with reverse osmosis systems. It is also preferred that the concentrations do not exceed 0.01 M neutral salt, 0.005 M acid salt, 0.0015 M surfactant, as higher concentrations may result in excessive corrosion in water systems having copper, mild steel and galvanized steel components. It is also preferred to add commercially available corrosion inhibitors (particularly copper inhibitors if the water system has copper components), anti-foaming agents (or foam thickeners, when a foam is desired for application in non-flowing water systems), and biocides in amounts indicated on the product labels, along with the treatment composition.

One advantage of composition and methods of the invention is that it effectively removes biofilm and scale that are not effectively removed by conventional prior art treatment protocols. The treatment composition improves overall treatment performance as a result of a synergistic interaction between the reagents of the composition. The treatment composition, preferably having reagents in solid form that are dissolved on site using the water in the system being treated, also decreases the costs and risks associated with shipping and handling large volumes of liquid treatment chemicals. Additionally, the methods of the invention provides optimal cleaning while minimizing damage to the materials that make up the water system being treated. The treatment composition and method are particularly beneficial in treating reverse osmosis systems in reducing energy consumption, increasing permeate flux, and extending the life of the membrane.

BRIEF DESCRIPTION OF THE DRAWINGS

The system and method of the invention are further described and explained in relation to the following drawings wherein.

DESCRIPTION OF THE PREFERRED EMBODIMENTS

Figure 1:
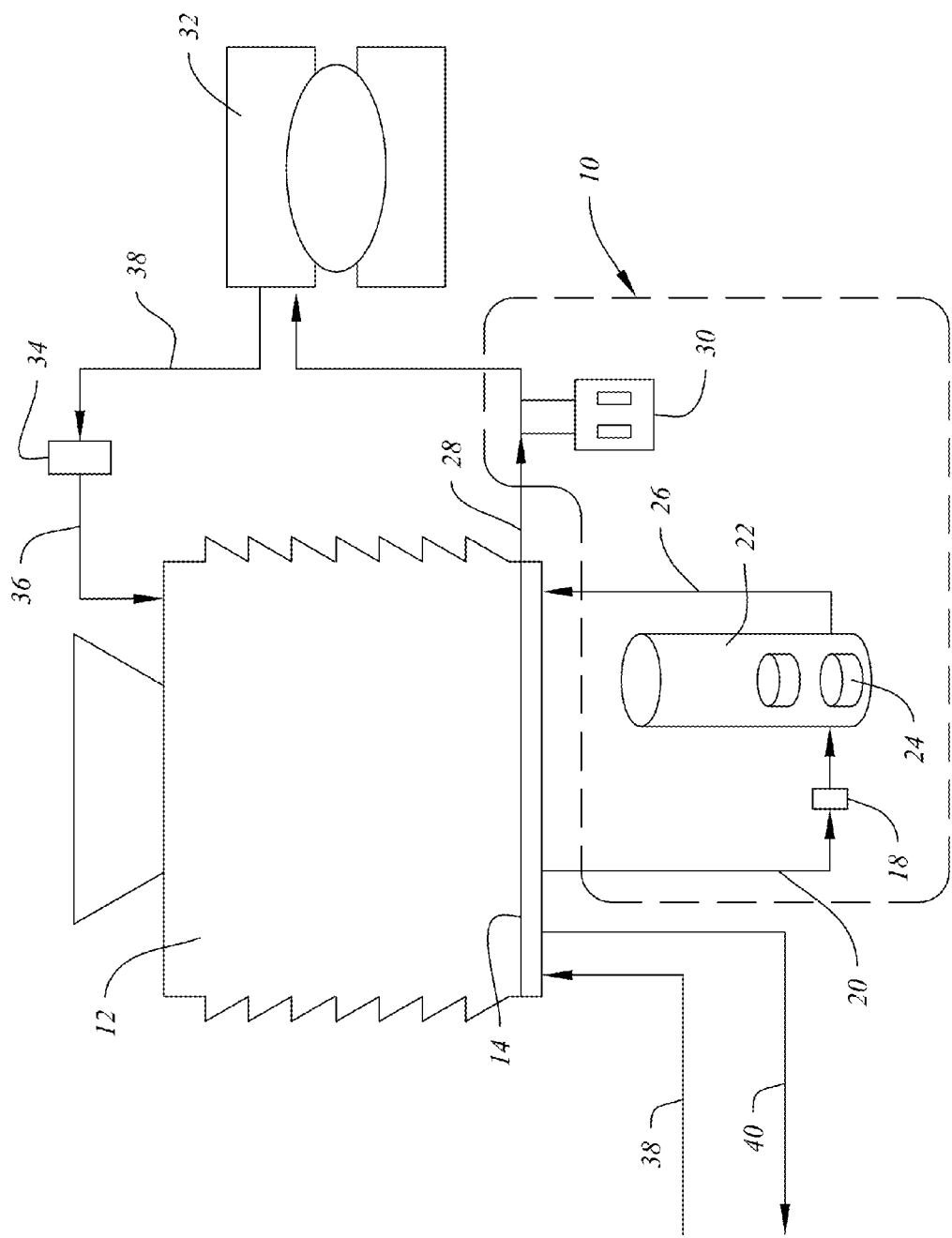
FIG. 1 is a side elevation view of one embodiment of a water treatment system according to the invention used with a flowing water system.

Referring to FIG. 1, one embodiment of a system 10 for treating a typically flowing water system, such as a cooling tower 12, according to a preferred embodiment of the invention is depicted. It should be noted that FIG. 1 is not to-scale, but the components of system 10 and the water system are depicted in a manner that allows them to be viewed on a single page. In normal operation mode of the cooling tower 12, water is circulated from the tower sump 14 through the condenser 32 then back into the top of the cooling tower 12. Water may be drained or bled from cooling tower 12 through drain line 40 and fresh water added through supply line 38, as needed. The system 10 preferably comprises a side stream 20 that diverts water from the sump 14 to a product feeder 22 or container that houses a solid chemical treatment product 24. The treatment product 24 may be in solid block form or may be in powdered form, and is most preferably the treatment composition of the invention, although other treatment products or chemicals may be used with system 10, including liquid chemicals. Alternatively, a source of fresh water (other than water from the water system) may be used to initially dissolve the treatment product prior to adding to the volume of water in the water system, but it is preferred to use water from the system itself. Water preferably passes through filter 18 prior to entering product feeder 22, but filter 18 may be located in another area of the overall process loop. Filter 18 is preferably used to remove biofilm agglomerates and other solids dislodged from the surfaces of the water system by the treatment composition. Any suitable filter mechanism or material may be used that will remove solids dislodged from the water system and prevent them from being re-deposited or colonizing or contaminating other areas of the water system. Most preferably, system 10 also includes a pressure monitor to measure the pressure differential across filter 18. The pressure differential aids in monitoring filter 18 to determine when the filter is fouled and needs to be replaced, which may be required one or more times during a treatment cycle.

During a treatment cycle, water from sump 14 contacts treatment product 24 inside product feeder 22. Any configuration may be used for product feeder 22 that permits water from the system being treated to contact and dissolve the treatment product; however, a feeder similar to that described in published U.S. patent application Ser. No. 12/787,025 is preferred. For smaller scale water systems, including drain systems, a timed-dosage feeder, similar to that described in published U.S. patent application Ser. Nos. 12/498,793 and 12/571,714 may also be used with modifications that will be apparent to those of ordinary skill in the art. Product feeder 22 is preferably used as both a container for holding the treatment product prior to a treatment cycle and a reservoir for mixing the treatment product with at least a portion of the water from the water system to form a slurry that is then mixed with the rest of the water from the water system. Alternatively, product feeder 22 may contain the treatment product and deliver it to a pipe or separate reservoir for mixing with the water or a portion of the water from the water system.

Once the water has contacted the treatment product 24, it begins to dissolve in the water and is carried out of the product feeder 22 through discharge line 26. Discharge line 26 then delivers the water with dissolved treatment product back into sump 14 where it is mixed with a larger quantity of water and the treatment product is further diluted. Water containing the treatment product is discharged from sump 14 through process stream 28, which preferably passes through a corrosion rack/corrosion monitor 30, where the level of corrosion in the water system may be monitored, then through evaporator/chiller/condenser 32, and finally through conductivity meter 34 before feeding the top of cooling tower 12. It is preferred that an electrochemical corrosion monitor to measure real time corrosion in the water system during treatment and/or a corrosion rack containing coupons of the reactive metals in the water system to monitor the corrosion rates be used as part of corrosion rack/corrosion monitor 30. Conductivity meter 34 may already be in place as part of the water system to monitor conductivity during normal operational cycling of water through the system. These monitors are common in cooling towers, such as cooling tower 12, and are frequently tied to automatic bleeding systems that bleed water from the system when needed. If not already part of the water system, conductivity meter 34 is preferably included as part of treatment system 10 and located near corrosion rack/corrosion monitor 30, although both the conductivity meter 34 and corrosion rack/corrosion monitor 30 may be placed at other locations within the overall water system. The water with dissolved treatment product then circulates through the cooling tower 12, back to sump 14, where a portion is again diverted through stream 20 to contact treatment product 24 in product feeder 22. The process is repeated until all of the desired treatment product is dissolved and circulated through the water system for sufficient time to contact substantially all the components of the water system, such as piping, fill material, and sump walls, remove scale build-up, biofilm and microbiological growth, and other corrosion by-products.

Alternatively, the treatment product 24 may be added directly to the sump 14 (or other water reservoir of the water system to be treated), rather than using side stream 20 and product feeder 22. In this embodiment, the treatment product is held in one or more containers, such as a drum or small tank, prior to the treatment cycle. If ingredients for the treatment product are held in more than one container, they may be mixed together prior to the treatment cycle, if desired. The treatment product is then mixed with at least a portion of the water from the system, or with another source of fresh water if desired, in one or more reservoirs, with the resulting mixture or slurry then being added to the water system to mix with the volume of water in the system. The reservoirs for mixing the treatment product with water may be the same as the containers for holding the treatment product or they may be separate. The reservoir may also be part of the water system itself, such as the sump of a cooling tower.

Regardless of how the treatment product is added to the water system, it is preferred that it be added so that the concentration of active agents in the total volume of water in the system is at least 0.001 M neutral salt, 0.0005 M acid salt, 0.00015 M surfactant, but not greater than 0.01 M neutral salt, 0.005 M acid salt, and 0.0015 M surfactant. Most preferably, the concentrations in the treated water are around 0.005 M neutral salt, 0.003 M acid salt, 0.00075 M surfactant. A corrosion inhibitor is also preferably used with the treatment product in a minimum amount of 2 ppm, and most preferably around 17 ppm. Other treating agents, such as a secondary biocide and anti-foaming agents, may also be added to the water system, either through side stream 20 or directly into sump 14 or other water reservoir in the existing water system, if they are not already included as part of the treatment product.

System 10 may also include other components, such as pumps, valves, and flow meters, which will be understood by those of ordinary skill in the art. System 10 may be permanently installed at a treatment site or may be portable and transported to a water system needing treatment as needed. If portable, treatment system 10 preferably includes quick connection ports for connecting system 10 to the process flow lines or water reservoir of the water system being treated. Similar connection ports may be permanently installed as part of the water system, if not already present, to allow easy periodic treatment of the water system using treatment system 10.

A treatment system similar to system 10 may also be used with non-flowing or non-circulating water systems, such as a drain or a tank. Preferably, the water system is capable of holding a volume of water for a period of time so that the treatment product may contact substantially all the contaminated components of the water system for effective treatment. With a drainage system, the piping may include valves that may be shut-off to stop the flow of water out of the drain, a clog may shut-off the flow of water, or an inflatable bladder may be inserted into the drain or pipe and expanded to shut-off the flow of water, all allowing the drainage system to temporarily hold a volume of water into which the treatment product may be added to be dissolved and diluted. An automated product feeder may be used to dispense treatment product into the non-circulating water system. Alternatively, a simple container may be used to hold the treatment product and used as a reservoir for pre-mixing the treatment product with water to dilute and dissolve it prior to introducing it into the water system. The treatment system may further include a mixer for agitating the water containing the treatment product within the water system to aid in contacting the treatment product with all components of the water system, if the water system does not already have such a mixer. In another embodiment, the treatment system may include piping and a pump to create a temporary circulating system during a treatment cycle.

A treatment composition according to one preferred embodiment, particularly suitable for use in circulating water systems (such as cooling tower) and larger scale non-circulating systems (such as large tanks), comprises chemical chelating agents (organic or inorganic acids and their corresponding neutral salts) and a surfactant. Most preferably, the acid is citric acid and the salt is sodium citrate. These chelating agents aid in metal ion sequestration from any biofilm, hard scale, and bulk water present in the water system being treated. The surfactant is preferably a cationic surfactant, and most preferably a surfactant with antimicrobial properties. Preferred surfactants include ammonium bromide compounds, ammonium chloride compounds, alcohol ethoxylates, and alcohol ethoxysulfates (AES). The surfactant aids in swelling and dissolving the extra cellular polysaccharide matrix that makes up a biofilm. In addition it can create an antimicrobial environment for microorganisms or water borne parasites that may be present in the water or biofilm environment. One or more commercially available corrosion inhibitors are also preferably included in the composition or separately added to the water system during a treatment cycle to protect the metallic components of the water system being treated.

A secondary biocide and an anti-foaming agent may also be used as part of the composition or separately added to the water system during a treatment cycle, and are preferably used, to provide an antimicrobial environment in the bulk water to prevent secondary contamination of the water source as biofilm agglomerates are sloughed off the primary biofilm surface being treated and to control foaming. These commercially available components are added according to product label specifications.

For the treatment to be effective it is preferred that the aqueous treatment solution, (i.e. treatment composition with the total water volume of the system being treated), have the following minimum concentrations: 0.001 M in the neutral salt, 0.0005 M in the acid salt, 0.00015 M in the surfactant, but concentrations not greater than 0.01 M neutral salt, 0.005 M acid salt, and 0.0015 M surfactant. The corrosion inhibitor(s) are used at the specified labeled usage rates, but preferably at least 2 ppm of corrosion inhibitors are used in or with the treatment composition. Additional corrosion inhibitors may be added if corrosion rates in the system are observed to increase during the treatment, which may vary according to the concentrations of the other components of the treatment composition and the duration of the treatment cycle. Most preferably, the concentrations in the treated water are around 0.005 M neutral salt, 0.003 M acid salt, 0.00075 M surfactant, and 17 ppm corrosion inhibitor.

In order to achieve the minimum concentrations of treatment composition described, and to allow the use of a wider variety of surfactants without the problems associated with the surfactant precipitating out of solution when the treatment composition is shipped as a concentrated liquid formula, it is preferred that at least one component of the treatment composition be in a solid form. Most preferably, all of the components of the treatment composition (and any other additives, such as corrosion inhibitors, secondary biocides, and anti-foaming agents) are in a solid block or powdered form that are dissolved and diluted by the water contained in the system being treated.

A treatment composition according to another preferred embodiment, particularly for use in non-flowing water systems, such as drainage systems, comprises the same chemical chelating agents (organic or inorganic acids and their corresponding neutral salts, preferably citric acid and sodium citrate) and a surfactant as previously described. These chemicals may be shipped to a treatment site in solid form, preferably as powders, for mixing with water at the site or may be shipped as a pre-mixed or ready-to-use liquid or foaming formulation. For the treatment to be effective, it is preferred that an aqueous treatment solution, (i.e. treatment composition with the total volume of water added or the total volume of water held in the drainage system if the flow of water is capable of being shut-off to contain a volume of water), have the following minimum concentrations: 0.001 M in the neutral salt, 0.0005 M in the acid salt, 0.00015 M in the surfactant, but concentrations not greater than 0.01 M neutral salt, 0.005 M acid salt, and 0.0015 M surfactant. In order to ensure the treatment composition reaches all contaminated surfaces, it is most preferably applied as an aerosol or a foaming formulation. A corrosion inhibitor, a foam thickener (as opposed to an anti-foaming agent for use in water systems such as cooling towers), and a propellant are preferably added to the treatment composition. Any compatible aerosol propellant may be used, although AB-46 is the preferred propellant. A secondary biocide may also be used.

The treatment composition will contain the chelating agents and surfactant in proper weight percentages to allow specified quantities to be added to a given volume of water to achieve the above concentration ranges. The chelating agents and surfactant may be pre-mixed in a solid block form or a mixed powder or a slurry prior to addition to the water system, or they may be separately added as either solid, liquid, or slurry components, depending on the type of water system being treated. Preferably, at least one of these components of the treatment composition is in a solid block or powdered form and most preferably, particularly for flowing water systems, the chelating agents and surfactant are pre-mixed into a solid block or a powdered mixture, where the solids are dissolved by the water in the system being treated. However, it may be beneficial to allow the surfactant to circulate through the water system (or otherwise contact the components of the water system) for a period of time to begin breaking down biofilms in the system prior to adding the chelating agents, so separate components may also be used. One or more corrosion inhibitors and a secondary biocide are preferably added to the water system being treated and anti-foaming agents or foam thickeners and a propellant, depending on the application, may also be added as needed. These additives may be in solid or liquid form, may be incorporated as part of a pre-mixed solid block or powdered mixture or pre-mixed or ready-to-use liquid, aerosol or foaming formulation along with the chelating agents and/or surfactant, or may be separately added at the treatment site as solids, liquids, slurries, or mixtures thereof.

A preferred method for treating a flowing water system according to the invention comprises the following steps: (1) bleeding or draining the water system to remove the existing water (if any) and any previous water treatment chemicals; (2) determining the total volume of water in the system (or the volume of water the system is capable of holding during normal operations for a circulating system or capable of holding to fill the system in a non-circulating system) and re-filling the system with water; (3) adding a treatment composition so that the final concentrations of active reagents in the water system are greater than 0.001 M neutral salt, 0.0005 M acid salt, 0.00015 M surfactant; (4) optionally adding corrosion inhibitors (typically 2 ppm minimum), anti-foaming agents or foam thickeners (depending on the water system), and/or a secondary biocide, as desired; (5) circulating the water with the treatment composition throughout the system (or contacting the water with the treatment composition with substantially all components of a non-circulating system) for a sufficient time; (6) periodically testing the system for corrosion products to monitor the corrosive effects of the treatment composition on the water system; (7) in a circulating system, filtering the water to remove dislodged solids and biofilm agglomerates; and (8) bleeding or draining the water containing the treatment composition from the water system after sufficient treatment time and removing any remaining solids in the sump or other water reservoir or low flow areas of the system (if any), then refilling with fresh water as applicable. This preferred method may also be used with non-flowing water systems, where the water system is capable of holding a volume of water for a given time. For example, this method may be used with a drain in which an inflatable bladder is inserted as a stopper and the drain pipe filled with a volume of water to allow the treatment composition to contact substantially all contaminated parts of the drain (from near the floor or basin in which the drain is installed down to a point at or near where the pipe joins another pipe or a trap). In such an application, the corrosion testing step may not be necessary.

With non-flowing water systems that are not capable of holding a volume of water, such as certain drainage systems, a preferred method comprises the following steps: (1) optionally flushing the water system with fresh water; (2) optionally preparing a liquid, aerosol, or foaming treatment composition at the treatment site so that the final concentrations of active reagents in the water system are greater than 0.001 M neutral salt, 0.0005 M acid salt, 0.00015 M surfactant based on the volume of water used to prepare the treatment (alternatively, the treatment composition may be shipped as a pre-mixed formulation); (3) applying the treatment composition to the water system by pouring, spraying, or foaming so that it contacts substantially all contaminated surfaces of the water system (such as the portion of a drain from near the floor or basin in which it is installed down to a point at or near which it joins another pipe or a trap); (4) optionally adding corrosion inhibitors (typically 2 ppm minimum) and/or a secondary biocide, as desired; (5) re-applying the treatment composition to the water system as needed so that the total contact time of the treatment composition with substantially all contaminated surfaces in the water system is sufficient; (6) optionally testing the system periodically for corrosion products to monitor the corrosive effects of the treatment composition on the water system; and (7) optionally flushing the water system with fresh water.

These methods result in a thorough cleaning of the water system, after which other water treatment regimens may be resumed and these methods utilized for periodic maintenance. Most preferably, the final concentrations of active reagents of the treatment composition in the water system are 0.005 M neutral salt, 0.003 M acid salt, 0.00075 M surfactant. A corrosion inhibitor, preferably TTA, at a concentration of at least 2 ppm and preferably at 17 ppm is added to the water system being treated to protect its components (particularly any copper components) from corrosion by the treatment composition chemicals. It is also preferred that the final concentrations of these reagents in the water system do not exceed 0.01 M neutral salt, 0.005 M acid salt, and 0.0015 M surfactant, as higher concentrations may result in excessive corrosion in water systems having copper, mild steel, and galvanized steel components. Most preferably, the method of the invention for flowing water systems is used with the solid block or powdered treatment composition and with the treatment system of the invention. Most preferably, the method of the invention for non-flowing systems is used with a pre-mixed or ready-to-use liquid, aerosolized, or foaming formulation of the treatment composition of the invention.

Prior to beginning the treatment, the volume of water in the water system, such as the cooling tower 12 in FIG. 1, is determined. Based on this volume, the amount of treatment composition needed to give the correct concentrations of active components as described above is placed in a container or mixing vessel that is transported to the treatment site. In another embodiment for water systems not capable of holding a volume or water, the treatment composition is preferably pre-mixed or ready-to-use in the proper concentrations. Alternatively, the treatment composition may be mixed at the treatment site by using any appropriate volume of water from outside the non-flowing water system, with it being preferred to use smaller volumes of water to reduce the reagents needed to give the preferred concentrations as additional treatments may be applied as necessary. If the water in the system (if any) contains high levels of cationic species, there is the potential that the chelating agents will be consumed before they reach the reaction zone. Therefore to minimize parasitic reactions the system should be bled to a point where the conductivity of the water in the system is the same value as the water being used to make up water loss resulting from normal operation. Alternatively, and particularly for smaller scale systems, such as drains and small tanks, the system may be completely drained prior to introducing the treatment composition.

After any necessary bleeding or draining of the system and re-filling with an appropriate volume of water (if the water system is capable of holding a volume of water), the treatment composition may be added to the water in the system. With larger scale circulating water systems, such as cooling towers, water from the system is preferably diverted through a side stream to the feeder, container, or mixing vessel housing the treatment composition, such as the use of side stream 20 and product feeder 22 in FIG. 1. As the water flows through the container/mixing vessel, the solid components of the treatment composition are dissolved and re-introduced into the water system where the treatment composition mixes with additional water to form the active product. Although it is preferred to use a side stream, the treatment composition can be mixed directly into any water system vessel or process stream (such as sump 14 or discharge line 28 in FIG. 1).

With non-circulating systems, such as drains, or smaller scale circulating systems, the treatment composition is preferably added directly to the water system rather than using a side stream, although a side stream may be added to an existing drain system if desired. The method of application may vary depending on the type of system involved, whether the system is capable of holding a volume of water (such as a tank or through the use of shut-off valve to hold water in a pipe) and the volume of water that may be held. For example, in a drainage system, the drain pipe may hold an appropriate volume of water to allow direct application of a solid, preferably powdered, treatment composition. The use of an inflatable bladder, inserted to a particular depth within the drain pipe, or a shut-off valve (if available and accessible) may be used as the shut-off mechanism to hold the water during the treatment cycle. Alternatively, a liquid treatment composition may be used and sprayed, aerosolized, or foamed into the drain or other water system. When smaller volumes of treatment composition are needed, the treatment composition may be shipped to the treatment site as a pre-mixed liquid, aerosol or foaming formulation. Although a pre-mixed formula is preferred, the treatment composition may be mixed at the treatment site with a given volume of water from outside the water system to form a liquid, aerosol, or foaming formulation which is then poured, sprayed, or otherwise added to the water system. A sprayed liquid, foam or aerosol application is most preferred when the water system is not capable of holding a volume of water. When mixed with water from outside the water system, deionized water is preferably used. Different spray nozzles, such as a directional sprayer or a long spray tube that is insertable in the opening of a drain cover, may be used to aid directing the treatment composition to all surfaces within the water system to be treated. Application of the treatment composition in a foaming formula is preferred for drain systems because the foam will expand to contact substantially all surfaces of the drain and will remain in contact with those drain surfaces for a longer period of time than most liquid applications, allowing time for the treatment composition to work on removing biofilms and other contaminants. Preferably, the foaming treatment composition is foamed into the drain line until a solid column is achieved from the base of the drain to the top of the drain.

The concentrations of reagents for the treatment composition used for non-circulating water systems are the same as for circulating water systems. When mixed with a volume of water held in the water system or with a volume of water in an external container are preferably between 0.001 M-0.01 M neutral salt, 0.0005 M-0.005 M acid salt, and 0.00015 M-0.0015 M surfactant, with these concentrations being determined based on the quantities of these reagents and the water, prior to addition of any other additives, such as corrosion inhibitors.

For either circulating or non-circulating water systems, other additives, such as corrosion inhibitors, anti-foaming agents (or foam thickeners and a propellant), and a secondary biocide may optionally be added through the side stream, product feeder, directly into the water system, or through an external container or sprayer, if these additives are not already part of the solid, powdered or liquid chemical materials containing the chelating agents and surfactant. These other additives are preferably added according to the product label specifications for each, as commercially available products. The order of addition of these chemicals and additives is not critical, but it is preferred that the corrosion inhibitor be added before or at the same time as the chelating agents and surfactant.

As the water system circulates the treated water (or the treated water is held within a non-circulating system or contacts the components of a non-circulating system), the dissolved treatment composition begins to contact the contaminated surfaces. The chelating agents attack any biofilm present on the surfaces and remove the metal bridging links that hold the extracellular polysaccharide matrix together. The surfactant and water penetrate the biofilm swelling it which in turn enables penetration of the chelating reagents to further break apart the matrix. As the extra polysaccharide matrix swells it sloughs off the outer exposed layers which are now soluble. It also sloughs of larger biofilm agglomerates which enter the bulk water flowing through the system. As the water flows, these agglomerates are transported to other areas of the system where they can settle out (particularly in low flow areas, such as the sump) and become a secondary source of contamination. The container/mixing vessel, side stream, or other process stream may be fitted with a filter to remove these biofilm agglomerates before they have a chance to reestablish colonies in the clean parts of the system. The water containing the dissolved treatment composition continues circulating through the water system (or being held within a non-circulating system) for a period of time to achieve effective cleaning of the water system. The duration of a treatment cycle will depend on factors such as the concentration of the active components of the treatment composition in the water system, the specific surfactant used, the flow rate of water through the system (or any mixing in a non-circulating system), and the degree or level of materials that need to be cleaned from the system, as will be understood by those of ordinary skill in the art. With larger circulating systems, such as cooling towers, the treatment cycle is typically 24-48 hours. With smaller scale systems, such as drains, the treatment cycle may be 5 minutes to a few hours. With drainage systems that do not hold a volume of water, the treatment composition may not fully contact all contaminated surfaces during an initial application or may not contact those surfaces for a sufficient period of time before draining from the system. As such, it may be necessary to do multiple treatments to achieve contact with contaminated surfaces for a sufficient time.

Many of the anthropogenic water systems use materials that can react with the chelating agents, the surfactant, or even the secondary biocide. As such, the system may be monitored for the formation of corrosion and corrosion by-products during treatment. It is preferred that an electrochemical corrosion monitor be used to measure real time corrosion in the system during treatment. Additionally, a corrosion rack containing coupons of the reactive metals in the system may be placed in the product stream to monitor the corrosion rates. The presence of the corrosion inhibitors should prevent many of the critical components of the system from being attacked. The range of concentrations for the active components of the treatment composition according to the invention should have minimal corrosive impact on the water system when used with suitable corrosion inhibitors; however, concentrations of active components of the treatment composition that are above the upper limit of the range (more than 10× the minimum values of 0.001 M neutral salt, 0.0005 M acid salt, 0.00015 M surfactant) may result in unacceptably high corrosion rates for long term treatment. At such high concentrations, the corrosion rates on mild steel, galvanized steel, and copper after 24 hours of treatment may be up to an order of magnitude higher than the acceptable limits. Additionally, these higher concentrations in the presence of galvanized steel in high laminar flow environments have been shown to produce a waxy coating that comprised the surfactant and the chelating chemicals. However, when using the treatment composition according to the invention at the minimum concentration values it was found that the corrosion rates on mild steel were lower than that observed with the known treatment compositions.

Many flowing water treatment systems use increasing conductivity (resulting from increased metal ion and carbonate concentration as the water is cycled) as an indicator and trigger to bleed off water and add fresh water. This practice helps prevent and slow down the formation of hard scale in the system. When the treatment composition is fully added to the water system according to the invention, the conductivity of the water will typically increase by 800 µS or 900 µS. This increase is normally sufficient to trigger the water system to bleed water to the drain, which would result in wasting the treatment composition before it has sufficient time to circulate through the water system for an effective treatment period. Therefore prior to adding any treatment composition to the water system, it is preferred to disable the bleeding mechanism for the system to prevent pre-mature discharge of the treatment chemicals.

In certain cases where flow is restricted or there is significant agitation there is the potential for the surfactant in the system to generate foam. To prevent foaming, an anti-foaming agent is preferably added to the system along with the treatment composition (if not already included as part of that composition). Secondary biocides may also be added, if not already included.

During a treatment cycle, circulating or otherwise moving water is preferably filtered to remove solids that are dislodged by the treatment. The filter should be monitored and replaced when it becomes fouled. This will be indicated by a visible soiling of the filter or by measuring an increase in pressure across the filter material. This helps prevent the filter material from becoming a secondary source of contamination that could result in further colonization of clean parts of the system. It is preferred that upon completion of the cleaning process the filter be removed from the system.

Upon completion of a treatment cycle, the water (including any remaining dissolved treatment composition and reactive reagents that have been spent during the process) should be evacuated from the water system. This helps prevent the deactivated organic load from becoming a secondary food source for microorganisms that will ultimately colonize the water system between treatment cycles. It is preferred that when cleaning is complete all the water in the system is dumped to the waste drain or receptacle. This will allow any solids that have settled the low flow areas to be removed from the system. Alternatively, a bleed valve activated by the water conductivity can be activated if present as part of the existing water system. This will drain the treatment composition and spent reagents from the system, however; there is the potential for low level residual treatment composition to remain for several weeks after the treatment is complete. After the treatment time has elapsed, the stopper can be removed and the liquid can be allowed to drain into to the main line and out to the waste treatment. Once the treatment time has elapsed, the sides of the walls will be sprayed with water which helps force the foam and broken up biofilm agglomerates down into the main drain lines and out to the waste treatment.

Once drained or bled, the water system may be refilled with fresh water (as applicable for flowing water systems) and normal operations resumed. Other treatment compositions, such as biocides and corrosion inhibitors, may be used during normal operations; however, it is preferred to periodically repeat the treatment method of the invention to thoroughly clean the water system as it has been found that even water systems appearing to be clean contain microorganisms, algae, and biofilms that are removed by the treatment composition and method of the invention.

The treatment compositions and methods for using such compositions according to the invention are further described and explained in relation to the following experimental examples:

Example 1: Treatment of biofilm contaminated coupons in the laboratory setting. Biofilm coupons containing multiple bacterial species were produced using a semi-batch bioreactor system in a laboratory setting. The biofilm reactor was designed around a continuous stir tank reactor and was fabricated using a 5 liter PVC container and contained 4 coupon holders and a central drive paddle that was used to induce a controlled fluid flow around the suspended coupons. The drive paddle was made from a Perspex paddle (10 cm×5 cm) that was attached to a 19 cm PVC rod and screwed into the drive of a gear DC motor with a gear ratio of 1:10 (Tanner Electronics). The coupon holders were also fabricated from PVC rods (14 cm) that were fixed in place through the lid if the biofilm reactor. The coupon rods were tapered at the bottom to enable easy fastening of both glass slides and metal coupons. Prior to operation, the reaction chamber and the individual components were disassembled, soaked in a 5% bleach solution then scrubbed in hot soapy water and rinsed in distilled water. Once cleaned the stir tank reactor was charged with 2 liters of reactor DI water and 20 g of the Free-Flow pellets containing bacteria (available from NCH Corporation or its divisions) was added to the water. Coupons were placed onto the coupon holding rods which were inserted into the Free Flow pellet material. The motor was connected to a RSR DC Power Supply Model HY3010E and the current set to 5 Volts giving a linear velocity of 0.4 feet per second across the face of the coupons. The reactor was run for 6 days with the Free Flow solution being replaced every 2 days. Standard microbiological assays showed that the system generated uniform biofilms with microbial populations exceeding $10^8$ CFU per ml of recovered supernatant.

These biofilm containing coupons were exposed to the treatment composition of the invention for 24 hours at three different concentration levels as follows:

Lowest concentration—0.0001M neutral salt (sodium citrate), 0.00005 M acid salt (citric acid), and 0.000015 M surfactant (tetradecyltrimethyl ammonium bromide);

Minimum concentration—0.001 M neutral salt (sodium citrate), 0.0005 M acid salt (citric acid), and 0.00015 M surfactant (tetradecyltrimethyl ammonium bromide); and Maximum concentration—0.01 M neutral salt (sodium citrate), 0.005 M acid salt (citric acid), and 0.0015 M surfactant (tetradecyltrimethyl ammonium bromide).

After the treatment, the slides were removed and the biofilm was processed to enumerate viable bacteria existing in the biofilm and also viable microorganisms in the supernatant liquid collected after processing. The results show that at the lowest concentration (10× below the recommended minimum concentration) there was no observable reduction in microorganisms in the biofilm or in the water showing that the biofilm was still viable (and growing). In the minimum concentration treatment, there was a 1 log reduction in the biofilm and the biofilm supernatant In the maximum strength treatment there were no recoverable microorganisms on the coupons or in the supernatant. The results are summarized in Table 1.

TABLE 1

Recoverable microorganisms at different treatment composition concentrations

| Slide | CFU/ml Recovered from Biofilm |
|---|---|
| Control (initial reading) | $1.0 \times 10^6$ |
| Control (after 24 hours) | $1.3 \times 10^7$ |
| Lowest Concentration (initial reading) | $2.8 \times 10^6$ |
| Lowest Concentration (after 24 hours of treatment) | $3.8 \times 10^7$ |
| Minimum Concentration (initial reading) | $5.0 \times 10^5$ |
| Minimum Concentration (after 24 hours of treatment) | $9.4 \times 10^4$ |
| Maximum Concentration (initial reading) | Below detection limit |
| Maximum Concentration (after 24 hours of treatment) | Below detection limit |

Example 1A: Example 1 was repeated again but in this case a commercially available secondary biocide, MB-2128, was added to aid the initial treatments. In this case it was observed that after processing the biofilm and supernatant at the lowest concentration treatment there was a 2 log reduction in the microorganism counts. For the minimum and maximum concentration levels there were no detectable microorganisms recovered from the biofilm or from the supernatant. The results are summarized in Table 2.

TABLE 2

Recoverable microorganisms at different treatment composition concentrations with a secondary biocide

| Slide | CFU/ml Recovered from Biofilm |
|---|---|
| Control (initial reading) | $1.0 \times 10^6$ |
| Control (after 24 hours) | $1.3 \times 10^7$ |
| Lowest Concentration (initial reading) | $8.5 \times 10^4$ |
| Lowest Concentration (after 24 hours of treatment) | $9.8 \times 105$ |
| Minimum Concentration (initial reading) | Below detection limit |
| Minimum Concentration (after 24 hours of treatment) | Below detection limit |
| Maximum Concentration (initial reading) | Below detection limit |
| Maximum Concentration (after 24 hours of treatment) | Below detection limit |

Example 1B: The process of Example 1 was repeated with the use of a commercial dispersant on the MB-2128 present in the same concentrations as Example 1A, but without the treatment composition of the present invention. When the treated solution and biofilm were processed it was found that there was only a 3 log reduction in the biofilm and supernatant were achieved.

The results of Examples 1, 1A, and 1B show that using the maximum strength concentration of the reagents was highly effective at removing biofilm and eliminating microorganisms in the solution and in the biofilm. The minimum concentration showed some efficacy at removing biofilm and reducing microorganisms when used alone; however; when the treatment composition was used with a secondary biocide there was a marked improvement in performance with no viable bacteria being recovered in the sessile or planktonic states. In addition the performance of the minimum concentration solution when used with the secondary biocide out-performed the commercial bio-dispersant when used with the same biocide, as shown by a comparison of Example 1A and Example 1B.

Example 2: Treatment of a pilot cooling tower with the minimum concentration reagents and the secondary biocide. In order to test the laboratory results on a larger scale, a study was conducted with a pilot cooling tower. A total volume of 28 gallons and a flow rate of 4 gallons per minute was used as the test system. The cooling tower had not been operational for over 1 year and a substantial biofilm had established in the pipes and hoses in the system. The sump was filled with municipal water and the pumps activated to start the flow of water. After 2 hours of operation water samples from the sump were collected and analyzed for the presence of microorganisms. In addition swab samples of the internal surfaces were collected and processed for microbiological analysis. The results of the analysis showed that water had $4 \times 10^2$ CFU per ml planktonic bacteria and $1 \times 10^6$ sessile bacteria. The microorganism analysis also showed that the biofilm was a multispecies form with a wide variation that represents a true consortia that would be found in real world environments.

The system was treated with the a concentrated solution of the citric acid, sodium citrate, and tetradecyltrimethyl ammonium bromide composition so that when all the components were added, the water in the system had the minimum reagent concentration of 0.001M, sodium citrate, 0.0005 M citric acid, and 0.00015 M tetradecyltrimethyl ammonium bromide. A secondary biocide, MB-2128, was added to give a final concentration of 200 ppm. When the reagents were added there was some foam forming at the air/water interface in the sump and some foam was observed at other points in the system. Samples of the water were collected after 1 hour, 24 hours, and 4 days. The results showed there was a half log reduction in the planktonic bacteria after 1 hour which increased to a 1 log reduction after 4 days treatment. Swabs of the biofilm in the hose showed that there was a 5 log reduction during this 4 day treatment time.

Visual inspection of the sump and hose reveled that biofilm had sloughed from the hoses and other system components during the process and were deposited in the low lying areas of the sump and in the inline filters. When analyzed this sump residue was shown to have $1 \times 10^3$ CFU per ml when re-suspended in buffer.

Prior to treatment the biofilm was a dark brown slime layer adhered to the surface of the pipes and tubes. When exposed to the treatment, it was observed that the biofilm color lightened and swelled after 2 days and finally got even lighter in color and began to detach from the surface and fall off in agglomerates. The most likely mechanism for these observations is that the exterior surface of the biofilm is attacked by the chelating agents and the surfactant dissolving the bridging metals that fix the extra polysaccharide polymers releasing them into solution and allowing the surfactant and water to penetrate further into the biofilm matrix. As the water, chelating reagents and surfactant penetrate the biofilm it swells, freeing up the interstitial spaces in the matrix lattice and thus allowing further penetration of the reactive agents. As the biofilm matrix swells it reaches a point where a combination of shear forces from the water flow combined with mechanical failure of the biofilm matrix causes agglomerates to slough of the walls and be dispersed into the bulk water. The discoloration of the biofilms during the treatment indicate that the color pigments are being removed or extracted from the biofilm matrix. This mechanism is further supported by the fact that the biofilm isolated in the sump and filter which is in essence a clone of the biofilm on the pipes had significantly fewer microorganisms indicating the ones in the outer layers of the matrix had been destroyed or extracted. Also, the continued presence of low levels of planktonic bacteria in the bulk water, when the lab studies indicate there should be none at these concentrations, infers a slow release of microorganisms over the treatment time, most likely from the breakdown of the biofilm matrix.

After the treatment, the pilot cooling tower system was flushed and the sump cleaned. The system was charged with a fresh water solution (no additional biocide treatment was added) which was circulated throughout the system. Samples were taken at the end of one week and processed for the presence of microorganisms. The plate count results were below the detection limit.

The cooling tower system was fabricated entirely from plastic components so a series of corrosion tests were performed to determine the effect of the process on copper and mild steel. A solution with the same concentration of reagents used in the pilot cooling tower was prepared and placed in corrosion pot test system. The solution was stirred continually for two weeks after which the coupons were removed and analyzed for corrosion. The results showed corrosion rate of mild steel to be between 0.5 and 1.0 mpy, which is below the accepted standard of 3.0 mpy. An industry standard corrosion inhibitor, when run in the same test, gave corrosion rates of 2.0 mpy. The copper coupons showed much higher corrosion rates of 1.2 mpy which is higher than the accepted standard of 0.2 mpy. When the experiment was repeated with 15000 MT, a different corrosion inhibitor commercially available from NCH Corporation or its divisions, added at recommended use concentrations, the copper corrosion rates decreased to 0.3 which is much closer to the acceptable industrial standard. It was determined that the presence of a copper inhibitor (present at a 2 ppm level) was sufficient to reduce copper corrosion and it also shows that the treatment composition does not react with this corrosion inhibitor at these concentrations. This compatibility enables these two products to be used together in a treatment program.

Example 3: Treatment of the Pilot Cooling Tower with the maximum concentration reagents and a secondary biocide. A second study was conducted with a second pilot cooling tower. Unlike the first study in Example 2, this pilot cooling tower had water in the system for 7 months. The internal surfaces of the pipes and tubing were covered in a tar-like black biofilm. The bottom of the sump had a number of deposits and the slide of the sump had a slimy feel indicating the presence of microbial growth. Microbiological analysis of the water in the sump and the biofilm showed $4 \times 10^5$ cfu per ml in the water and $2 \times 10^7$ cfu per cm$^2$ in the biofilm on the sump. In addition, analysis of the microorganism population showed a much greater diversity in species when compared to the microorganisms in Example 2. The pilot cooling tower was treated with the a concentrated solution of the citric acid, sodium citrate, and tetradecyltrimethyl ammonium bromide so that when all the components were added to the water in the system, the reagent concentration was at the maximum level of 0.01M, sodium citrate, 0.005 M citric acid, and 0.0015 M tetradecyltrimethyl ammonium bromide. A secondary biocide, MB2128, was added to give a final concentration of 200 ppm. Samples of the sump water were collected at 24 hours and after 4 days and a swab of the biofilm were collected after 4 days.

Analysis of the sump water showed that the planktonic count in the bulk water was below the detection limit after 24 hours and remained below the detection limit for the remainder of the experiment. It was noted that there was some growth on plates that were plated using 50 μL samples which indicates that there are small agglomerations of biofilm in the bulk water that are protecting the microorganisms as the biofilm sloughs off the surfaces and these are released in the plating process. As with Example 2, the biofilm coloration lightened from black to a very light brown color. Swab samples on the thin areas of the biofilm produced counts that were below the detection limit and swabs taken in areas of biofilm that were thicker resulted in counts of $2 \times 10^2$ cfu per cm$^2$.

Figure 2:
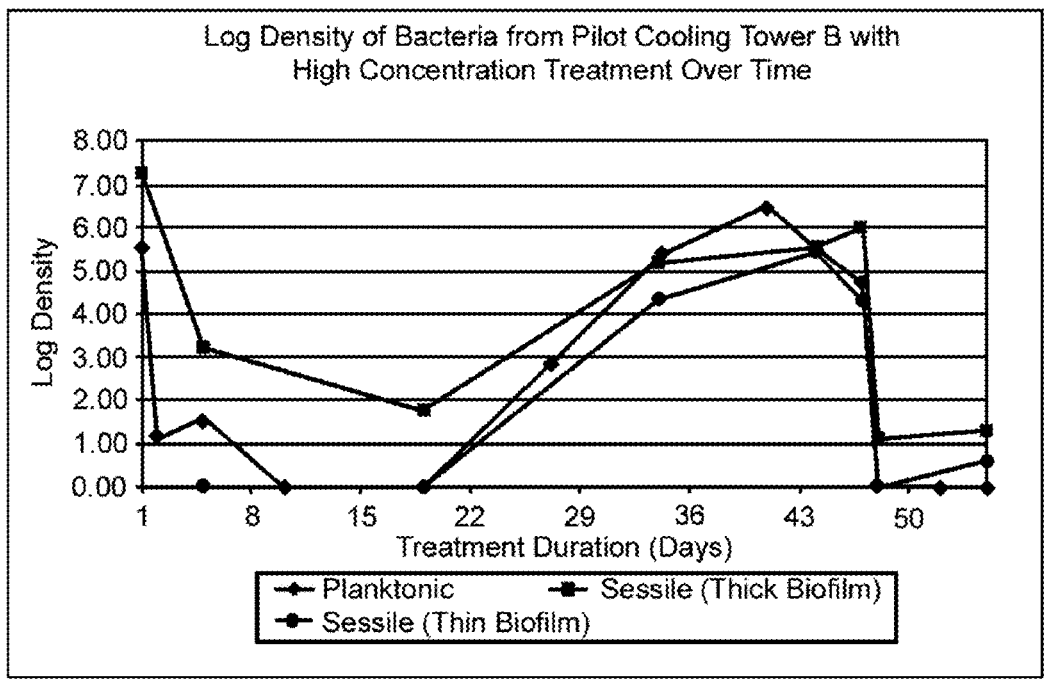
FIG. 2 is a graphical plot of log reduction in planktonic and sessile bacteria resulting from treatment with maximum concentration treatment composition.

Once the experiment was complete the system was drained, and refilled with fresh water that was circulated throughout the system. Unlike Example 2, the solids that were sloughed off during Example 3 remained in the sump and other low flow areas. During this time water loss resulting from evaporation was made up by the addition of fresh water. During the experiment it was noted that there was foam present on the surface of the water in the sump. Microbiological samples were collected on weekly intervals of the sump water and the results of the analysis are shown in FIG. 2. The chart in FIG. 2 shows that for about 20 days after treatment, the microbial population in the system remained under control. However, there was a rapid increase in both sessile and planktonic bacteria over the next 10 days bringing the populations of both up to the normal starting level again. These results indicate that a biofilm is reestablishing itself on the surface of the tubing. Because the pilot cooling tower was not drained and re-filled with fresh water after the treatment cycle was complete, it is believed that the planktonic microorganisms utilized the organic load left over from the treatment composition as a food source, as indicated by the bacterial high counts in the bulk water. Bleeding or draining the system after the treatment cycle was complete, and removing any remaining solids from the sump, would have removed most of this organic load, resulting in the system remaining under control for a longer period of time.

Example 3A: Treatment of the pilot cooling tower with the maximum concentration reagents in powdered form and a secondary biocide. At day 48, the cooling tower of Example 3 was treated again, this time with the maximum concentration reagents in powder form. This example demonstrates that there was no difference in performance between the power and liquid treatment compositions. As shown in FIG. 2, within three hours of the addition of the treatment composition in powdered form, both sessile and planktonic bacteria were reduced to levels below the detection limit and they remained at these low levels for over 1 week.

Corrosion evaluations on the maximum concentration for the treatment composition were performed on coupons in the corrosion rack in the cooling tower and in pot tests as previously described. The corrosion coupons in the coupon rack showed signs of corrosion after 24 hours. However, the galvanized steel coupons developed a waxy build up on the surface that increased in thickness with reaction time. The deposit was found to be a combination of the sodium citrate, citric acid, and the surfactant. It also contained zinc, copper and iron. This deposit was only observed on the zinc coupon in the coupon rack. Other zinc coupons that were placed in the sump, which is a low flow environment, did not show any sign of this waxy build up. The results from the corrosion pot tests showed that without the addition of the 15000 MT corrosion inhibitor, the corrosion rates were 30 mpy for mild steel and 4 mpy for copper. It was also noted that a waxy deposit formed on both the copper and mild steel coupons which had the same spectrum as that found on the zinc coupon in the tower. Corrosion rates with the addition of 15000 MT were unchanged for mild steel, however; copper corrosion rates were decreased by an order of magnitude to 0.4 when the 15000 MT corrosion inhibitor was used.

The results from these Examples help define how this treatment composition can be applied to treat real anthropogenic water system based on overall performance and reactivity. The treatment composition works by reacting with the biofilm in a synergistic chemical and physical interaction that causes it to slough or exfoliate from the surface it is attached to. As it breaks from the surface it forms small agglomerates that contain viable microorganisms. Failure to remove the biofilm agglomerates dislodged as a result of the treatment can lead to rapid re-colonization of the system. The minimum concentration treatment requires several days to act; however; corrosion rates are low especially when used with a corrosion inhibitor. The higher concentration treatment requires a shorter exposure time up to 24 hours, however, it is highly corrosive to the metals in the system. The higher concentration treatment has the potential to form a thick waxy build up in galvanized surfaces in areas where there is high laminar flow. The addition of corrosion inhibitors is preferred, especially for water systems that contain copper. Adding the reagents in powder form significantly reduces the volume of material required for the treatment without negatively impacting the efficacy of the treatment.

Example 4: Treatment of a 600 gallon cooling tower. This Example was designed to apply the laboratory results to a small scale cooling tower in the field. This example was carried out on a CTS model 2125, 125 ton cooling tower with a total volume of 600 gallons located on the campus of a local University. The cooling tower was used to cool the computer building and was operating with a full heat load for the duration of the test.

Prior to performing the test the cooling tower was being treated using a conventional biocide protocol. The conventional biocide treatment was stopped two weeks prior to the treatment using the treatment composition and method of the invention. Water samples were collected and analyzed prior to the treatment to give base line readings. The condition of the system was also documented photographically. It was noted that the water in the system was clear; however, a thin film of algae was growing on the bottom of the sump. There were no signs of other deposits in the sump. The fill material had a black film formed throughout the entire structure. The film was a mixture of biological and inorganic compounds. Swab testing showed a microbiological load of $2 \times 10^6$ cfu per $cm^2$. Analysis of the sump gave an initial count of $1 \times 10^2$ cfu per nil with the majority of the microorganisms identified as *pseudomonas* spp. Dissolved and suspended copper were within acceptable ranges as was the dissolved and suspended iron.

Prior to initiating the treatment, the cooling tower system was flushed, fresh water added, then the bleed valve was disconnected from the conductivity controller. For protection of the copper in the chiller system, a tolyltriazole (TTA) compound was added to give a total of 9 ppm in the bulk water and this was circulated through the system for 1 hour. A treatment composition comprising citric acid, sodium citrate, tetradecyltrimethyl ammonium bromide solids (in powdered form) were weighed out in amounts that when added to the water in the cooling tower would give a final concentration of 0.005 M sodium citrate, 0.003 M citric acid, and 0.00075 M tetradecyltrimethyl ammonium bromide. The powders for each component were added to a drum and mixed together to generate a uniform blend. Water from the sump was mixed with the solids in the drum and the resulting slurry was introduced directly into the sump of the cooling tower. Secondary biocide, MB2128, was added directly to the sump at the recommended use levels. An in line filter was placed over the exit pipe from the cooling tower to the condenser during the treatment cycle to filter out solids dislodged by the treatment.

Once the compound was added a thin layer of foam formed where the water falling from the fill hit the water in the sump. As the product circulated it was noted that the water changed from colorless to semi-transparent grey and it was no longer possible to see the bottom of the sump. The product circulated for 48 hours, then the cooling tower system was dumped and fresh water was added and the conventional biocide program reinstated.

Figure 3:
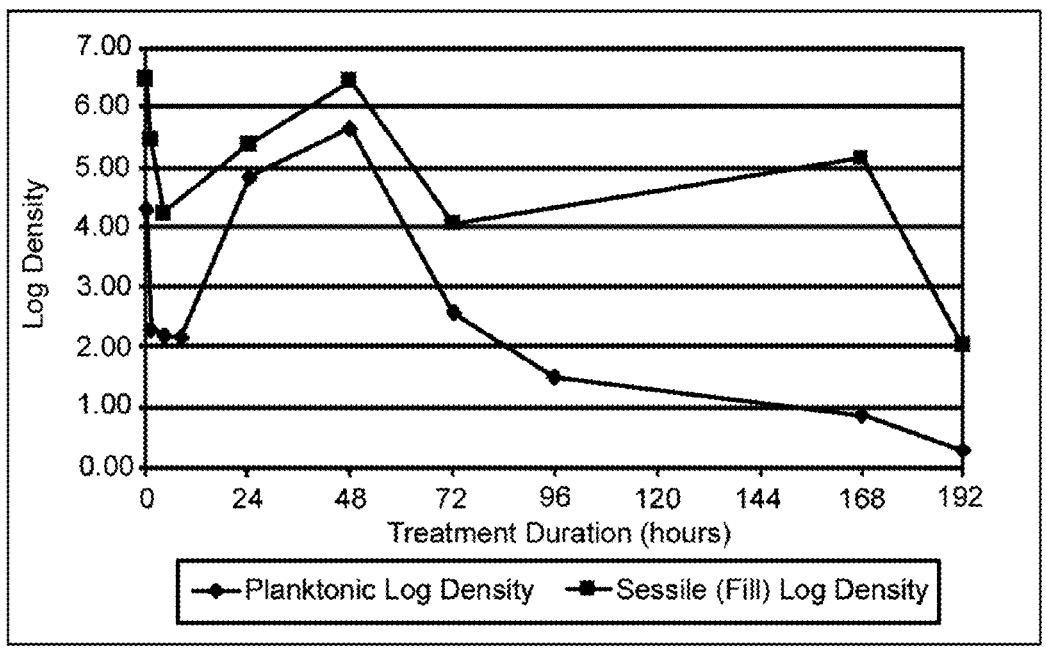
FIG. 3 is a graphical plot of planktonic and sessile bacteria isolated from the cooling tower as a function of time.

FIG. 3 is a graph of the planktonic and sessile bacteria isolated from the sump and fill during the experiment of Example 4. The graph shows that immediately after the addition of the treatment composition there was a drop in the viable bacteria load in both planktonic and sessile forms. However, it was observed that at 24 hours (for the planktonic bacteria) and 48 hours (for the sessile bacteria), the number of viable bacterial had increased to the almost the original values. The microbiological analysis showed that in the initial measurements the colonies looked like normal *pseudomonas* spp. but after 24 hours a second species originally thought to be contamination began to appear on the plates. When these species were identified they were found to be a *pseudomonas* spp that was different from the first ones observed. Additional analysis showed that there were protozoa species present in the water that were not present in the initial analysis. With the addition of the conventional biocide after the treatment there was a significant drop in the number of viable planktonic and sessile bacteria in the cooling tower system.

During the treatment in Example 4, it was observed that the black biofilm on the fill material was loosened and began to fall off into the sump. A spray of water taken from the sump was used to remove the remaining material from the fill material.

A green/grey deposit was observed on the filter. Analysis of the deposit material showed it to have the following composition: Organic 37%, Calcium Carbonate 18.5%, Silica 31% with the remaining being zinc, aluminum and iron oxides.

As observed with the other Examples, the treatment discolors the biofilm, swelling it and causing it to slough of in agglomerates and to delaminate from the surfaces of the water system. The results also show these agglomerates contain viable bacteria and that these bacteria can re-colonize the system, even when an in-line filter is in place to remove the solids. However, the results show that addition of another secondary biocide after the bio-dispersion treatment (in addition to the amount of MB2128 that was added to the sump at the beginning of the treatment) is effective at reducing the viable microorganisms in the planktonic and sessile state.

Figure 4:
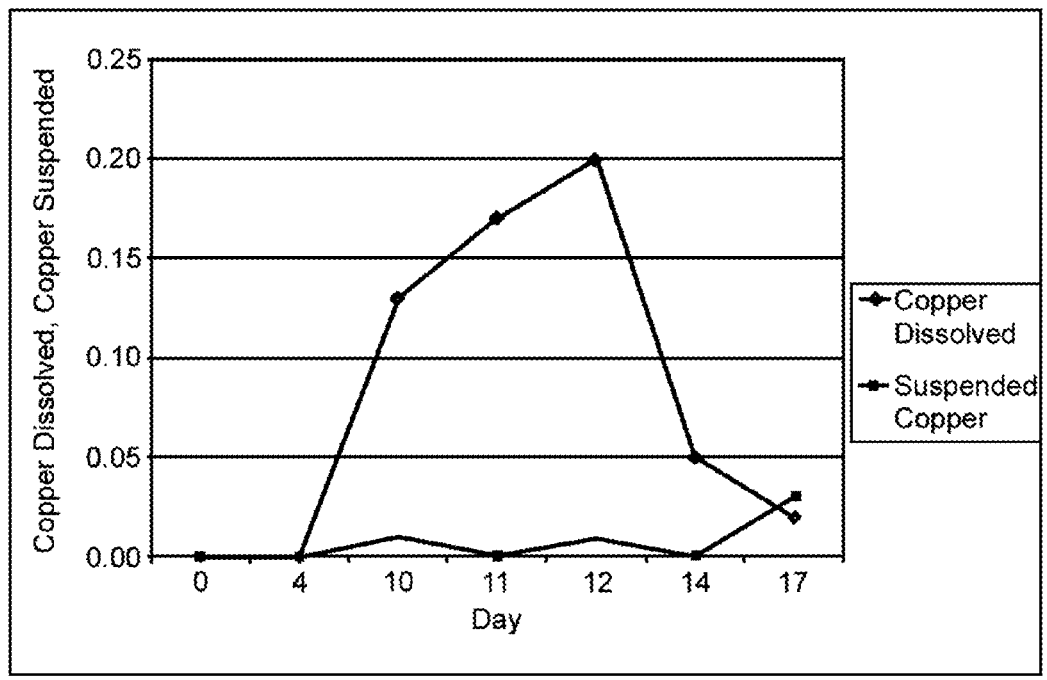
FIG. 4 is a graphical plot showing dissolved and suspended copper in the bulk water as a function of time.

FIG. 4 is a graph showing copper dissolved and suspended in the bulk water of the cooling tower before, during, and after the treatment. The graph shows that prior to the treatment, the copper levels in the system were essentially zero. On the day the test was started the copper levels began to climb and they remained high even after the 48 hour treatment cycle was completed and the water containing the dissolved treatment composition was flushed from the system. However, the values returned to the normal low levels after several days of normal operation. These results indicate, as observed in the prior Example, in that long term exposure (such as a treatment cycle of 48 hours or longer) of cooper to the treatment composition could be detrimental to the water system performance and/or copper components of the water system. As such, it is most preferred to use a copper corrosion inhibitor with the treatment composition to prevent excessive corrosion.

An additional benefit of the treatment according to this embodiment of the invention is that it seemed to be effective at removing or discoloring algae from the sides of the sump. The results from the field experiment in Example 4 showed that when used in a controlled manner and following the procedures outlined above this treatment composition is effective at removing biofilm, scale, and algae.

Example 5: Treatment of a 700 gallon cooling tower. Another experiment was conducted on a cooling tower that was considered to be a clean tower. A Marley 700 gallon cooling tower was identified and inspected for signs of visible contamination. It was noted that the water was clear, there was some brown deposits on the fill in the water, and there was a small amount of calcium carbonate scale on the outer surfaces of the fill. One week prior to starting the experiment, the conventional biocide treatment program was stopped. Microbial analysis of the water and brown deposit on the fill prior to starting the experiment showed counts of $1\times10^4$ cfu per ml and $1\times10^4$ cfu per cm, respectively, which are well within the specifications for this tower to be considered clean.

The treatment composition concentration was the same as that used in the previous experiments with the only change being the surfactant, which was switched to didecyldimethyl ammonium chloride. Prior to treatment a 17 ppm tolytriazole solution, a copper corrosion inhibitor, was added to the sump and was allowed to circulate for 1 hour. After the hour had elapsed, the surfactant was added directly to the sump of the cooling tower and it was allowed to circulate for 24 hours. After 24 hours the other reagents were added.

It was observed that with the initial addition of the surfactant the water turned turbid but within 24 hours it had turned clear again. There were no signs of deposits or other material present in the water. With the addition of the other reagents the liquid began to turn green around the edges of the sump where the fill was located.

After 4 hours of treatment the system was set to bleed and the tower was filled with fresh water. The next day when the tower was inspected it was found that there was a significant amount of foam built up inside the tower. The foam had a considerable amount of green material over the surface. Most notably in the bottom of the sump was a light green deposit that was not there the previous day. Although the deposit looked like it was a copper oxide or a copper compound, it was determined to contain 92% organic material with the remainder being zinc oxide and calcium carbonate upon analysis. This indicated that the cooling tower contained more organic material than initially appeared by visual inspection and the water analysis and that the treatment was effective at removing organic material from the surfaces of the tower Because of the time of the year and the low heat load on the system the water did not cycle as quickly as expected so even after the blown down process there was still citrate and surfactant in the system. This became problematic as the continued action of the reagents released more organic material into the sump of the cooling tower, which may then re-contaminate the system. Irregular flow patterns through the system lead to excessive foaming which required treatment with antifoam.

Figure 5:
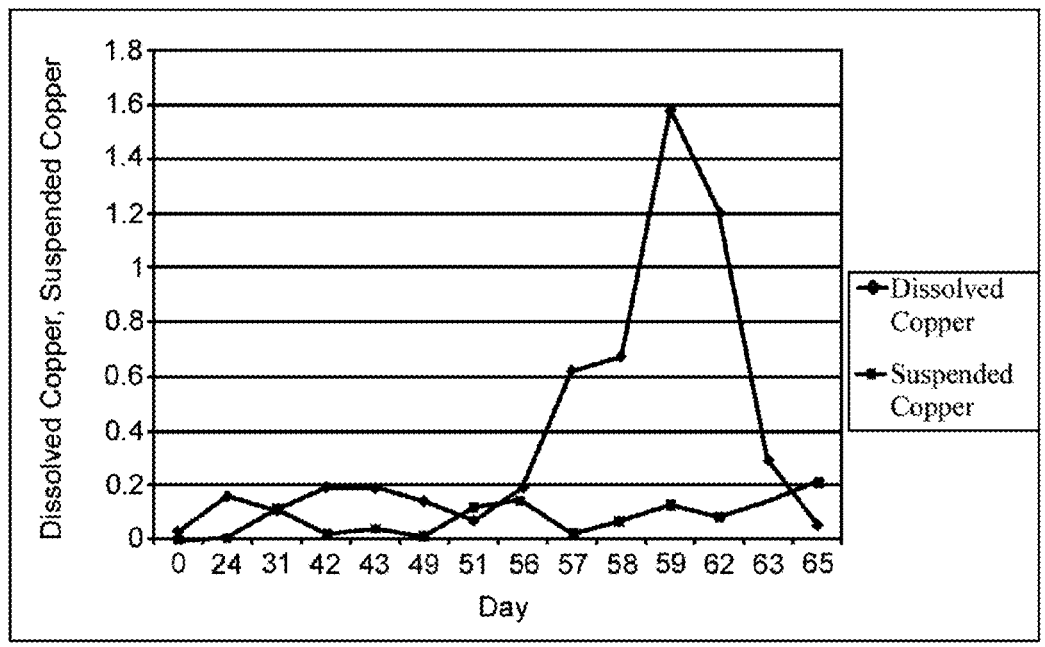
FIG. 5 is a graph showing dissolved and suspended copper as a function of time.

Additionally, the presence of the citrate and surfactant reagents in the system even after the system was bled, resulted in further corrosion of the copper elements of the system. FIG. 5 is a graph showing the dissolved and suspended copper in the cooling tower system. Even after the cooling tower system had been flushed, there was a continued dissolution of the copper in the system and that rate of corrosion is excessive. In order to prevent permanent damage to the cooling tower system the entire unit was bled, and power washed before being filled up with fresh water. Analysis showed that after this process the copper levels returned to normal. Accordingly, it may be necessary to rinse or clean the water system after bleeding or draining the water system upon completion of the treatment cycle to fully remove the reagents prior to filling the system with fresh water.

Figure 6:
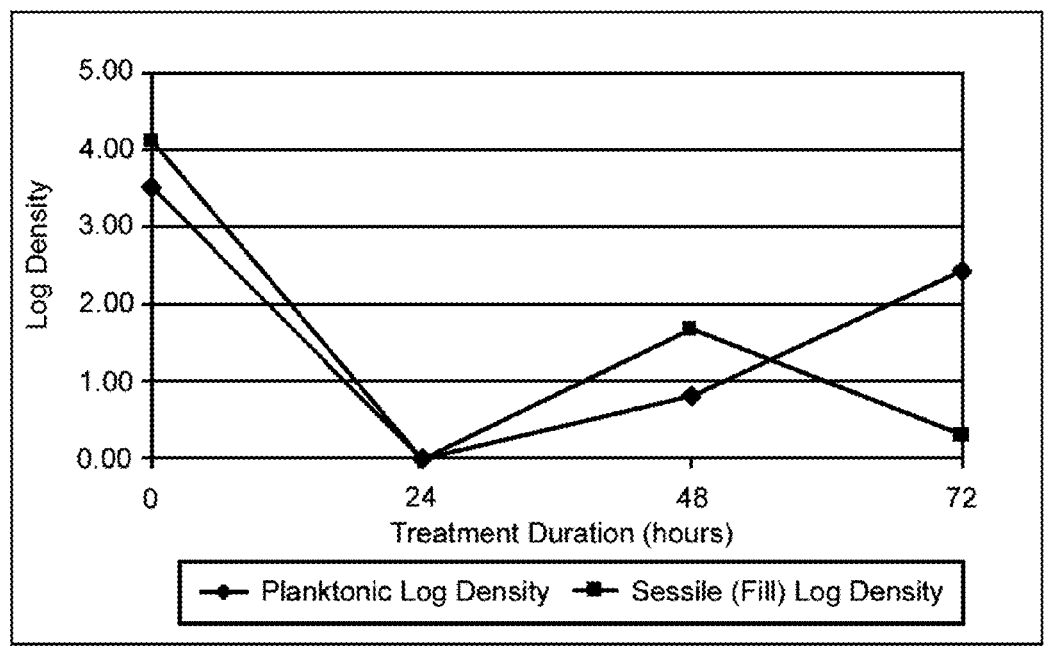
FIG. 6 is a graph showing the planktonic and sessile bacterial counts in Example 5.

FIG. 6 is a graph showing the planktonic and sessile counts from the tower in Example 5. As expected, there is an initial decrease in the planktonic and sessile counts; however, as more of the biofilm material is released into the sump and the concentration of treatment composition is decreased as the reagents are consumed and with the initial bleed, the number of viable microorganisms began to increase again.

Example 6—Treatment of a 3,500 Gallon Cooling Tower. In another study, a cooling tower with a volume of 3,500 gallons was treated with a composition according to the invention. The treatment was prepared with the neutral salt and organic acid being mixed together in small containers (1-5 gallon capacity) and the surfactant being pre-prepared in a separate container. Prior to adding the treatment composition, 265 g of the tolytriazole was added to the water system, followed by 795 g of an antifoaming agent. The treatment composition was then added to the sump by adding 3.5 gallons of the neutral salt/organic acid mixture, followed by 3.5 gallons of the surfactant. The solution was allowed to mix and the final concentration of the reagents in the water was 0.005 M sodium citrate, 0.003 M citric acid, and 0.00075 M didecyldimethyl ammonium chloride.

After addition of both parts of the treatment composition, a thin layer of foam started to form in the sump. The highest level of foam was in proximity to the make-up valve which was the area of the most turbulence. Also, a thin layer of foam formed where the water falling from the fill splashed into the water level in the sump. As the reagents circulated through the system, the water became slightly hazy and the bottom of the sump was not as visible. The water also turned turbid at the pour point of the surfactant addition, but it cleared up during the treatment cycle.

Dissolved and suspended copper were monitored before and during the treatment cycle. The dissolved copper level climbed up to about 0.2 ppm during treatment and quickly dropped once the bleed valve had been opened. Suspended copper level remained about the same during treatment cycle. Because the treatment composition is corrosive to copper, the addition of a copper corrosion inhibitor, such as tolyltriazole is preferred.

An ATP analysis, based on the detection of Adenosine Tri-Phosphate which is present in living (viable) cells, was used in this Example to determine the biological load in the water system. The detection of ATP indicates the water system contains living cells. An ATP analysis may also detect non-cell bound ATP released in the bulk water, but such non-cell bound ATP has a very short life-time and quickly degrades outside of the cell. When biofilms are present within a water system there is typically a rapid rise in the total ATP following biodispersant addition. The rise in total ATP is due to biodispersant transferring cells from the surfaces of the water system into the bulk water. Once biocide is added to the system, it kills circulating biofilm as well as newly-exposed layers of the biofilm adhered to the surfaces of the system and a convergence of total ATP can be detected. In this Example, the total ATP was tested before, during and after the treatment cycle. Total ATP went up to 4200 RLU when the treatment composition was added into the system, suggesting circulating biofilm in the bulk water. Once MB-60B (a secondary biocide) was added to the system, the total ATP quickly dropped back to its initial values as measured prior to addition of the treatment composition.

The results of the field trials are summarized as follows: (1) The treatment composition and method are best used in cooling towers or water systems where there is a high water exchange due to heavy heat loads; (2) the treatment composition will attack copper present in the water system being treated (such a copper tubing in the chiller units of a cooling tower), so the use of a corrosion inhibitor is preferred; (3) the treatment composition is effective at removing organic, biological and inorganic materials that have built up on the surfaces of the water system; (4) once the treatment cycle is complete, returning to a conventional biocide treatment is an effective way to keep the microbial populations under control, but repeated, periodic treatments with the treatment composition and method of the invention are preferred; (5) the use of the reagents in the treatment composition in powdered form is effective; (6) the reagents in the treatment composition can be added directly into the sump or other water reservoir and diluted with the water already in the anthropogenic system being treated; (7) the treatment will release agglomerates into the system that contain microorganisms that are normally not present in the bulk water system; and (8) the biofilm agglomerate can be effectively removed from the system with the use of an inline filter.

Example 7: Treatment of *legionella* biofilms. A *Legionella pneumophila* (ATCC 33153) biofilm was grown in the CDC reactor under 4 days of continuous buffered charcoal yeast extract media supply. A rod with three stainless steel coupons was then sampled for viable cell counts prior to treatment exposure. Additional rods were transferred to batch reactors containing either buffered dilution water (control coupons), minimum concentration reagents or high concentration reagents of the treatment composition according to the invention. After 1 hour and 24 hours, a rod was pulled from each reactor and sampled for viable cell numbers. There was a 1.4 and a 2.4 log reduction in *legionella* in a biofilm for the minimum and maximum treatment concentrations, respectively.

Example 8: Foaming Treatment of a Dialysis Drain at Maximum Concentration. Another study was conducted using a foaming treatment on a dialysis drain at a local hospital. A solution with a concentration of active reagents comprising 0.01 M sodium citrate, 0.005 M citric acid, and 0.0015 M Neodol 91-6 as the surfactant was prepared using deionized water. A 300 ml aliquot of the solution was transferred into an aerosol can in combination with Neodol 91-6 (in addition to the Neodol 91-6 used as the surfactant component of the treatment composition, which was added to improve the foaming properties), sodium benzoate (a preservative as a corrosion inhibitor), AMP-95 (an extra foamer), and 20 g of AB-46 (a propellant). The aerosol can was fitted with a foaming nozzle and stem, sealed, and then pressurized. The can should be fitted with a nozzle that will best deliver the treatment composition to substantially all surfaces in the drain, which will depend on the structure and physical configuration of the drain being treated. Any compatible surfactant may be used, although Neodol 91-6 is preferred. A high foaming surfactant is best for the aerosol application in order to extend contact time as long as possible.

Upon arriving at the treatment site, the tube connecting the dialysis machine and the drain was removed and placed in a biohazard bag. The drain cover was removed and the drain was inspected visually and photographically for the presence of deposits and biofilm. The inspection revealed the presence of a dried waxy build up and biological growth on the sides of the drain leading to the main drain line. Microbiological samples inside the drain at the water-air interface were taken before and after treatment.

The treatment composition was applied to the drain as a foam from the aerosol can, in a manner that completely filled the drain line from the water level to the top of the drain line. As the foam broke, additional treatment composition was applied to maintain the foam column height. The foam remained in the drain line for 1 hour after which it was washed away using a hand held sprayer charged only with tap water. It was noted that at the end of the treatment, biological debris were present in the foam and when it was rinsed with water, the sides of the drain walls looked visibly cleaner. It was also noted that the foul odor emanating from the drain was considerably less at the end of the treatment. Once the foaming treatment was complete, the system was treated with a regular maintenance dose of a conventional, commercially available drain treatment product.

Example 9: Foaming Treatment of a Dialysis Drain at Minimum Concentration. A second study on the dialysis drain was conducted using a treatment composition having to the minimum concentrations of 0.001 M Sodium Citrate, 0.0005 M Citric Acid, and 0.00015 M surfactant. The treatment composition was applied to the drain as a foam in a manner that completely filled the drain line from the water level to the top of the drain. There was no difference in the consistency of the foam when compared to Example 8. As the foam broke, additional treatment composition was applied to maintain the foam column height. The foam remained in the drain line for 1 hour before being flushed from the line with tap water, then treated with a conventional, commercially available drain maintenance chemical program. As with Example 8, the sides of the wall of the drain line looked cleaner and there was a reduction in the bad odor coming from the drain line.

Example 9A: Liquid Treatment of a Dialysis Drain at Minimum Concentration. A third study was conducted to compare a liquid treatment composition to the foaming composition of Example 9. A solution of the treatment composition without the additional aerosol agents was prepared to give an active concentration of 0.001 M Sodium Citrate, 0.0005 M Citric Acid, and 0.00015 M surfactant. The drain line was opened and an inflatable drain plug was inserted to reach the bottom of the drain line. The plug was connected to an air pump and inflated to 40 psi causing it to seal the drain. The liquid treatment composition was poured down the drain and left to react for 1 hour. After the treatment time had elapsed, the plug was deflated and the liquid was allowed to run down into waste. The walls of the drain line were washed with tap water and a conventional, commercially available drain maintenance product [was then added. In addition to the visible reduction on contaminants within the drain after the treatment, swab analysis showed that there was a reduction of microorganisms on the drain line wall after the treatment.

The results of the experiments show that both the liquid and foam applications are effective at cleaning biological material from the walls of the drain lines. However, the experimental observations showed that the foam exposed the surface to fresh active chemical through the action of the foam breaking and also seemed to help physically remove the biological soil from the surface of the drain line.

Table 3 shows the results of microbiological analysis of swab samples collected from the sides of the drain walls in Examples 8 and 9. Two swabs, labeled A and B, were taken for each drain and for each application of the foaming treatment composition, at the maximum concentration and the minimum concentration. A treatment composition according to one embodiment of the invention was applied, followed by an application of commercially available Drain Tain, then the swabs were taken at different locations on substantially opposites sides of the drain. These results showed that the microorganism count was reduced by an average of 5 logs for both treatment compositions.

TABLE 3

Microorganisms from Drain Walls

| Drain No. | Treatment | Sample | Before Treatment CFU/mL | After Treatment CFU/mL |
|---|---|---|---|---|
| 1 | Drain-Tain (Prior-Art Treatment/Control) | Swab 1A | $2.00 \times 10^1$ | $5.00 \times 10^0$ (Below limit of quantitation) |
| 1 | Drain-Tain (Prior-Art Treatment/Control) | Swab 1B | $9.75 \times 10^7$ | $1.00 \times 10^1$ Below limit of quantitation |
| 2 | Example 9 (Min. Conc.), followed by Drain-Tain | Swab 2A | $1.88 \times 10^7$ | Below limit of detection |
| 2 | Example 9 (Min. Conc.), followed by Drain-Tain | Swab 2B | $2.20 \times 10^2$ | $1.18 \times 10^1$ (Below limit of quantitation) |
| 3 | Example 9 (Min. Conc.), followed by Drain-Tain | Swab 3A | $4.20 \times 10^5$ | $1.5 \times 10^2$ (Below limit of quantitation) |
| 3 | Example 9 (Min. Conc.), followed by Drain-Tain | Swab 3B | $2.71 \times 10^3$ | Below limit of detection |
| 4 | Example 8 (Max. Conc.), followed by Drain-Tain | Swab 4A | $5.65 \times 10^8$ | $1.29 \times 10^3$ |
| 4 | Example 8 (Max. Conc.), followed by Drain-Tain | Swab 4B | $7.50 \times 10^8$ | $9.85 \times 10^4$ |
| 5 | Example 8 (Max. Conc.), followed by Drain-Tain | Swab 5A | $2.50 \times 10^1$ (Below limit of quantitation) | $1.05 \times 10^2$ (Below limit of quantitation) |
| 5 | Example 8 (Max. Conc.), followed by Drain-Tain | Swab 5B | $1.30 \times 10^1$ (Below limit of quantitation) | $2.00 \times 10^1$ (Below limit of quantitation |

Example 10: Treatment of Waterless Urinals. Another study was conducted using the foaming treatment composition to remove and prevent the reoccurrence of biological build up in waterless urinal systems. Prior to adding the treatment composition, the drain plug leading from the urinal to the drain was removed revealing a layer of biological and inorganic deposits at the air-liquid interface. The drain line was filled with the foaming product delivered from an aerosol can with a concentration of active ingredients 0.01 M sodium citrate, 0.005 M citric Acid, and 0.0015 M didecyldimethyl ammonium chloride. The treatment was allowed to react for 5 minutes after which the foam was rinsed with water and a conventional sealer was added. The control urinals had the drain line brushed and conventional sealer added. The first week after treatment there were no visible changes in the condition of the sealer or odor control blocks. The second week, the untreated urinals started to show signs that the odor control systems were breaking down. The urinals to which the foaming treatment composition was applied had fully functional odor control systems and were odor free. After week three, some of the odor control blocks in the untreated urinals started to exhibit biological growth and the sealer was changing color from blue to green, whereas the treated urinals showed little to no biological build up. After 4 weeks the odor control systems in the untreated urinals had broken down completely, while the treated urinals were still fully operational and exhibited controlled odors.

In additional to the previous results, the results of these drain and urinal examples are summarized as follows: (1) the foaming treatment composition is preferred for use in cleaning drain systems because it is easier to apply to substantially all contaminated surfaces in drain systems and the physical breaking of the foam helps mechanically remove biological based material from the walls of the drain system; (3) the treatment composition helps eliminate foul odors in drain systems; (4) the treatment composition may extend the lifetime of a clean, unclogged drain, especially in the case of the waterless urinals; (5) the treatment composition is preferably allowed to contact the surfaces of a drain system for 5-120 minutes, but a contact time of around 60 minutes is most preferred; (6) the treatment composition eliminates or minimizes food sources/harborages for invertebrate insects within drain systems; (7) the residual effects of the treatment help prevent biofilm from growing back in drain systems.

Figure 7:
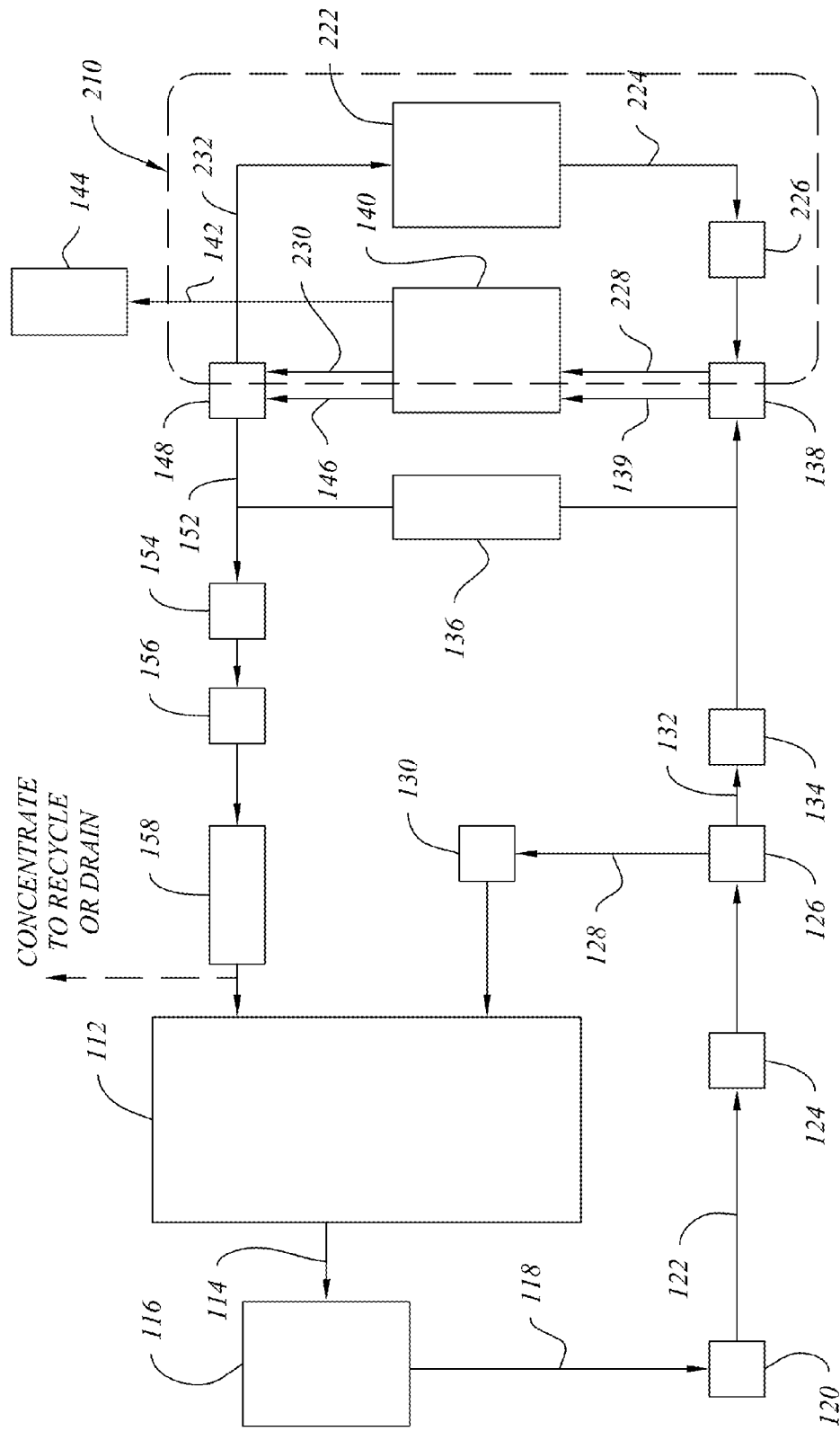
FIG. 7 is a schematic of one embodiment of a reverse osmosis treatment system according to the invention.

Referring to FIG. 7, one embodiment of a treatment system 210 for treating a reverse osmosis system according to a preferred embodiment of the invention is depicted. It should be noted that FIG. 7 is not to-scale, but the components of system 210 and the water system are depicted in a manner that allows them to be viewed on a single page. Treatment system 210 preferably comprises a line 232 to divert water from the reverse osmosis system to a treatment feeder 222, with treated water being returned to the reverse osmosis system through line 224 via pump 226. Pump 226 may also be located on line 232 or in a treatment feeder tank. Treatment feeder 222 may be as previously described for feeder 22 where a solid or powdered treatment product is dissolved for feeding into the reverse osmosis system. It is preferred that a solid or powdered treatment product be used, but a liquid product may also be used. For purposes of the experiments described below, feeder 222 is a tank containing a submersible pump 226 and dissolved treatment product. Three way (or other multi-way) valves 138 and 148 control the flow of water to and from treatment system 210 from the reverse osmosis system. Separate flow lines 146 and 230 exiting membrane cell 140 and flow lines 139 and 228 entering membrane cell 140 are shown on FIG. 7, but these are preferably a single line exiting and a single line entering membrane cell 140 with flow direction (such as to line 152 or 232 upon exiting the membrane) being controlled by valves 148 and 138.

In normal operation mode of the reverse osmosis system or primary loop, water containing a solute (such as salt water) is circulated from a holding tank 112 (or other source of water) to a reverse osmosis membrane cell 140. A high pressure piston pump 116 pumps water from tank or source 112 through line 114 and discharges the water through line 118 to a pulsation dampener 120, then through line 122 to a flow switch 124. From the flow switch 124 the water continues to pass through a pressure relief valve 126, through line 132 to a pressure gauge 134, and a differential pressure transducer 136. Pressure relief valve 126 and a bypass valve 130 are installed as safety regulators for system pressure overload. Water may be diverted through line 128 and valve 130 back to the tank or source 112, or to the drain or another storage tank, as needed. When not diverted, the water then flows through valve 138 to line 139 to enter the reverse osmosis membrane cell 140. In experimental set-ups described below, the reverse osmosis membrane cell was a Sterlitech CF042D with a polyamide flat-sheet membrane (Toray 82V), but treatment systems according to the invention may be used with other reverse osmosis membrane systems. The membrane cell 140 separates the water stream into a purified permeate flux stream 142 and a concentrated stream 146. The permeate stream 142 is collected in a permeate tank 144 or sent to another system for further processing, use, or storage. The concentrate stream 146 is typically discharged to the drain or recycled to another system for use as shown by the dashed line on FIG. 7. For the experimental set-up, the concentrate stream 146 was recycled back to the source tank 112 for reuse, to conserve water during the experiments. The concentrate stream then passes through a concentrate pressure gauge 154 and a back pressure regulator 156. The back pressure regulator 156 controls feed and concentrate pressure for the total system. From the back pressure regulator 156, the concentrate flow passes through a high pressure flowmeter 158 and returns back into the bulk tank 112 (or is otherwise recycled or sent to the drain).

During a treatment cycle, some water is diverted from the reverse osmosis system to the treatment system 210 as described above. The water containing the treatment product may circulate only through a smaller secondary loop of treatment system 210 to treat only the reverse osmosis membrane cell 140 (from stream 228 through cell 140 out through stream 230 to feeder 222 and back around) or may be circulated through the primary loop of the entire reverse osmosis system to treat all of the piping and components exposed to the water that may be contaminated with biofilm. Since biofilm may develop on piping and components throughout the reverse osmosis system, it is preferred to treat the whole system. In a typical reverse osmosis system where the concentrate stream 152 would be recycled to another process or sent to the drain, a bypass may be installed to allow the concentrate water containing treatment product to continue on to line 114 and through the whole reverse osmosis system or primary loop, as will be understood by those of ordinary skill in the art. Most preferably, the treatment composition is added as a single dose at the beginning of the treatment cycle. When a solid treatment composition is used, the single dose may take some time to be fully added to the reverse osmosis system being treated as it may take several cycles of water recirculating through the secondary loop and feeder 222 to fully dissolve the treatment product to obtain the desired concentration of treatment product in the reverse osmosis system. Once the dosage of treatment composition has been added or fully dissolved, then the water containing the treatment composition may circulate through only the primary loop of the reverse osmosis system (using valve 148 to shut-off circulation through the secondary loop of treatment system 210 until the next treatment cycle when a new dose of treatment composition is added), or may continue circulating through only the secondary loop if treatment of only the reverse osmosis membrane is desired. The water containing the treatment product is circulated through the entire reverse osmosis system (or a portion thereof) for sufficient time to contact substantially all the components of the reverse osmosis system (or a portion thereof), such as piping and the membrane, to remove biofilm and microbiological growth. The duration of a treatment cycle may vary according to the size of the reverse osmosis system, characteristics of the water in the reverse osmosis system and degree of fouling.

Alternatively, the treatment composition may be continuously added over a period of time during a treatment cycle, may be batch added in several discrete doses during a treatment cycle, or a combination thereof. When continuous addition or several batch doses in a single treatment cycle are desired, some water is diverted through valve 148 to treatment system 210 to add more treatment product back in through line 228 and some water, containing treatment composition, passes through valve 148 (or a separate valve, if desired) back into the reverse osmosis system to line 152 during the entire treatment cycle or at periodic intervals during a treatment cycle. The water with dissolved treatment composition then circulates through the reverse osmosis system back to the membrane cell 140, where additional treatment product may be added through line 228. The process is repeated until all of the desired treatment product is dissolved and circulated through the reverse osmosis system for sufficient time to contact substantially all the components of the reverse osmosis system, such as piping and the membrane, to remove biofilm and microbiological growth.

A filter may be added anywhere in the reverse osmosis system or the treatment system 210 to remove dislodged solids and biofilm agglomerates. The duration of a treatment cycle will vary depending on the concentration of treatment composition added to the reverse osmosis system, but will typically be between 2 to 5 hours at a minimum concentration of 255 ppm of treatment composition based on the volume of water in the reverse osmosis system and treatment system 210. Treatment cycles are periodically repeated to maintain the reverse osmosis system and control biofilm growth. System 210 may also include a controller, such as a programmable logic controller, to control operation of pump 226 and/or any valves, such as 138 or 148, to allow water to flow through treatment product feeder 222 or to otherwise add treatment composition into the reverse osmosis system by initiating a treatment cycle. Alternatively, components can be connected to an existing controller for the reverse osmosis system, if there is one, to initiate a treatment cycle. Treatment cycles may be set up to automatically repeat at periodic time intervals, such as every 48 hours or other interval depending on the reverse osmosis system, or may be triggered by reverse osmosis system parameters, such as increased system pressure or increased heat from pumps in the reverse osmosis system as an indicator that the membrane is fouled and needs to be treated.

System 210 may also include other components, such as additional pumps, valves, and flow meters, which will be understood by those of ordinary skill in the art. System 210 may be permanently installed at a treatment site or may be portable and transported to a reverse osmosis system needing treatment as needed. If portable, treatment system 210 preferably includes quick connection ports for connecting system 210 to the process flow lines of the reverse osmosis system being treated. Similar connection ports may be permanently installed as part of the reverse osmosis system, if not already present, to allow easy periodic treatment of the water system using treatment system 210.

A preferred treatment composition for use with treatment system 210 comprises a first chelating agent, a second chelating agent or other ingredient that will react with the first chelating agent (or another ingredient) to produce a second chelating agent, and a surfactant. The treatment product or composition preferably comprises these ingredients as a pre-mixed composition in proportions such that when added to the volume of water in the reverse osmosis system (or volume of water in the portion thereof being treated, such as the volume of water in the secondary loop for treating the membrane or the volume of water in the primary loop for treating the whole system), the concentrations are between 0.001 M and 0.01 M of the first chelating agent, 0.0005M and 0.005 M of the second chelating agent, 0.00015 M and 0.0015 M of the surfactant. Most preferably, the first chelating agent is an organic acid (preferably citric acid), the second chelating agent is a salt of the organic acid (preferably sodium citrate, preferably generated by adding citric acid and sodium bicarbonate to the composition as reactants to generate sodium citrate, but the salt may also be directly added as a separate ingredient), the surfactant is an anionic surfactant (preferably sodium diisopropylnaphthalene sulfonate or Aerosol OS). Ammonium bromide or ammonium chloride compounds may also be used as surfactants. Most preferably, the treatment product contains all of these ingredients and is in solid or powdered form, but liquids may also be used. A preferred solid treatment composition is made by mixing around 42% acid and around 52% sodium bicarbonate (to react with the acid to produce sodium citrate when added to the water in the reverse osmosis system). Since the treatment composition may be diluted with other ingredients, particularly if provided as a liquid, it is preferred that the ratio of active ingredients be around the amounts described above to provide preferred concentrations of active ingredients when added to the water in the reverse osmosis system. Additionally, these ingredients may be separately added to the reverse osmosis system in amounts that provide the above concentration ranges in the water in the reverse osmosis system. Regardless of how the treatment product is added to the reverse osmosis system, it is preferred that it be added so that the concentration of active agents in the total volume of water in the reverse osmosis system is the ranges above.

One or more of the other ingredients used for treating circulating water systems and/or drains discussed above, such as corrosion inhibitors and a secondary biocide, may also be used for treating reverse osmosis systems. Most preferably, a corrosion inhibitor is added before the treatment composition is added and in an amount to achieve a concentration of 1 ppm to 5 ppm in the water of the reverse osmosis system. Most preferably, a secondary biocide is added after the treatment composition is added and in an amount to achieve a concentration of 1 ppm to 40 ppm in the water of the reverse osmosis system. It is most preferred to add any secondary biocide after the treatment composition has been circulating through the reverse osmosis system for around an hour or longer.

A preferred method for treating a reverse osmosis system according to the invention comprises the following steps: (1) determining the total volume of water in the reverse osmosis system (or the volume of water the system is capable of holding during normal operations); (2) adding a treatment composition (preferably as described above) so that the final concentrations of active reagents in the reverse osmosis water system are greater than 0.001 M of a first chelating agent, 0.0005 M of a second chelating agent, 0.00015 M surfactant; (the ratio of neutral salts and acid salts may be generated by reacting sodium bicarbonate with citric acid and the concentrations of these three active ingredients are more preferably in the concentrations ranges described above); (3) optionally adding corrosion inhibitors (typically 2 ppm minimum), anti-foaming agents or foam thickeners (depending on the water system), and/or a secondary biocide, as desired; (4) circulating the water with the treatment composition throughout the reverse osmosis system (or circulating the water with the treatment composition through a portion of the reverse osmosis system to contact the membrane) for a sufficient time; (5) periodically testing the system for corrosion products to monitor the corrosive effects of the treatment composition on the water system; (6) filtering the water to remove dislodged solids and biofilm agglomerates; and (7) bleeding or draining the water containing the treatment composition from the reverse osmosis water system after sufficient treatment time and removing any remaining solids in the sump or other water reservoir or low flow areas of the system (if any); (8) rinsing the water system to remove any remaining treatment composition prior to resuming normal operations; and (9) restarting the reverse osmosis system to resume normal operations until the next treatment is needed. In one preferred embodiment, a corrosion inhibitor is added an allowed to circulate through the reverse osmosis system for a period of time, preferably around 1 to 5 hours, prior to adding the treatment composition. In another preferred embodiment, the surfactant is added and allowed to circulate through the reverse osmosis system for a period of time, preferably around 1 to 5 hours, prior to adding the first and second chelating agents (or other ingredient that reacts to produce the second chelating agent). In yet another preferred embodiment, the treatment composition is added and allowed to circulate through the reverse osmosis system for a period of time, preferably around 1 to 24 hours, prior to adding the secondary biocide.

Upon completion of a treatment cycle, the water (including any remaining dissolved treatment composition and reactive reagents that have been spent during the process) should be evacuated from the reverse osmosis water system. This helps prevent the deactivated organic load from becoming a secondary food source for microorganisms that will ultimately colonize the water system between treatment cycles. It is preferred that when cleaning is complete all the water in the reverse osmosis system is dumped to the waste drain or receptacle. This will allow any solids that have settled the low flow areas to be removed from the system. It is also preferred to rinse the reverse osmosis system to remove any remaining treatment composition prior to resuming normal operations. Once drained or bled and rinsed, normal operations for the reverse osmosis water system may be resumed. Other treatment compositions, such as biocides and corrosion inhibitors, may be used during normal operations; however, it is preferred to periodically repeat the treatment method of the invention to thoroughly clean the reverse osmosis system as it has been found that even water systems appearing to be clean contain microorganisms, algae, and biofilms that are removed by the treatment composition and method of the invention.

The treatment compositions and methods for using such compositions according to the invention are further described and explained in relation to the following experimental examples. An experimental reverse osmosis system and treatment system 210 was set up using small tanks for the source water (112) and treatment product feed (222), as shown in FIG. 1. The reverse osmosis system, or primary loop between tank 112 around to reverse osmosis membrane cell 140 and back to tank 112 was inoculated with the bacterial species, Bacillus megaterium. The treatment or secondary loop pulling water from reverse osmosis membrane cell 140 through line 232, through treatment product feeder 222, through line 228 back to the membrane, was set up to only treat the membrane for purposes of these experiments. Most preferably, the entire reverse osmosis system would be treated by circulating water containing treatment product, preferably in the concentrations indicated above, for a treatment cycle.

The bacteria was inoculated in a 9 ml vial of tryptic soy broth (TSB) aseptically, then placed in an incubated shaker for 18 hours at 35° C. This was completed every 48 hours, four times total for each experiment performed. Before the start of each experiment, 12 gallons of tap water were filtered through a granulated activated carbon (GAC) in-line filter cartridge before it was added to the primary loop tank 112. Then B. megaterium was inoculated into the primary tank 112 once the system was online. After the initial inoculation at the start, subsequent inoculations of B. megaterium occurred every 48 hours. This procedure was followed with all control experiments and experiments with product treatments.

The feed pressure (Pf) and the concentrate pressure (Pc) were set to 300 psi by adjusting the back pressure regulator 156 and the bypass valve 130. The reverse osmosis system's flowrate was set to 1 gpm (gallon per minute) and observed to correlate any fluctuations with biofouling on the reverse osmosis membrane in cell 140. Permeate flux was collected in tank 144 during the overall experiment for a total of 166.5 hours, but was not collected during treatment cycles. A scale was used to determine the total mass of the permeate flux. The high discharge rate of the piston pump 116 results in a higher total system temperature. A chiller and a pump were installed (not shown in FIG. 1) to help maintain a constant total system temperature around 78° F. to 80° F. An additional safety feature was setup to initiate the power to the piston pump 116 and chiller pump. A heat flux sensor was also installed to monitor piston pump's motor as an additional safety device. It was set to activate if the motor temperature reached 175° F. or higher, and would then turn the pump off. This was done to prevent any over-heating issues with the pump's motor and to prevent any fire hazards. A programmable logic controller (PLC) was installed to control the operation of both pumps, the flow switch 124 on the feed line, and a heat flux sensor for the piston pump's motor 116. The pressure relief valve 120 was preset to 600 psi as a safety regulator for the total system. This was done to prevent any pressure gauges being overloaded past their maximum point and to help decrease major pressure swings from the piston pump on the total system. The chiller is activated once the piston pump 116 comes online. The temperature of the chiller is set to 75° F. to help maintain the primary bulk tank 112 temperature at 78-80° F. The flow switch 124 on the feed line of the primary loop was set to activate if the system flowrate dropped below 0.1 gpm. This was done to prevent any damage to system materials and prevent flooding by the system. Additional skids were placed under the bulk tank 112 as a secondary containment for flooding prevention as well.

For each experiment, the Pf, Pc, differential pressure (AP), piston pump temperature, primary bulk tank temperature, chiller temperature, flow rate, and permeate flux were recorded daily and monitored indications of biofouling on the reverse osmosis membrane. Pictures of the membrane were taken at the beginning of each experiment, at 48 hours, at 96 hours, and at 144 hours for both the control (untreated) and treated experiments. For treated experiments, there were three doses of a treatment composition according to a preferred embodiment of the invention added into the reverse osmosis system through the secondary treatment loop (to treat only the membrane for purposes of this experiment). The first dose was added at 48 hours, the second at 96 hours, and the final treatment at 144 hours. Each treatment cleaned the reverse osmosis membrane for a duration of 2 to 5 hours and then the reverse osmosis system was set back to circulate through the primary loop to simulate normal operations.

The treatment composition used in the experiments comprises around 43.1% citric acid, around 5.2% Aerosol OS (a surfactant), and around 52.2% sodium bicarbonate. The concentration of treatment composition used was 255 ppm (of all ingredients as a single composition combined), which is the lowest concentration that has proven efficacy. Throughout each experiment, water samples of the primary bulk tank 112 and of the permeate water 144 were collected. Swabs of the membrane in cell 140 were taken before and after each treatment randomly; each swab area was 1×1 cm$^2$ and the swab was inserted into a conical vial containing 1 ml of sterile buffer (Butterfield) solution. Microbiological analysis was performed on each sample recovered.

Concentrations of the bacteria from the primary bulk water, permeate water, and from the membrane before and after treatments were determined by serial dilutions. 1 ml of sample was diluted in 9 ml of Butterfield buffer and dilutions were carried out 5 times to give a final dilution of $10^{-5}$. Dilutions were plated on Tryptic Soy Agar (TSA) and incubated overnight at 35 C. Plates that grew 30-300 colonies were counted the following day and back calculations were made to determine total colony forming units (CFU) per ml. Standard Gram staining was performed on the samples as well to provide a qualitative analysis of the bacteria.

Figure 8A:
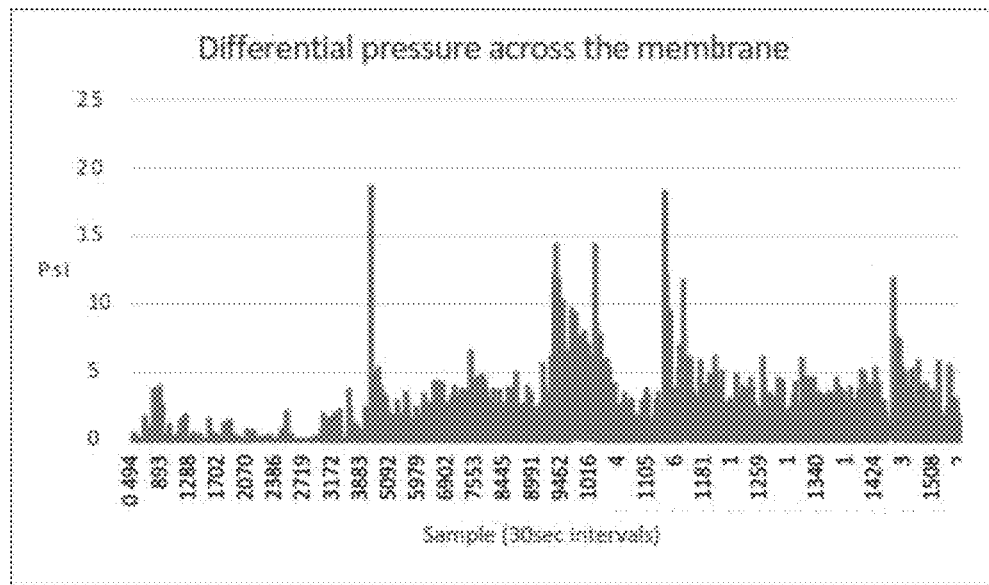
FIG. 8A is a graph showing raw data for the pressure differential across a reverse osmosis membrane during one experiment.
Figure 8B:
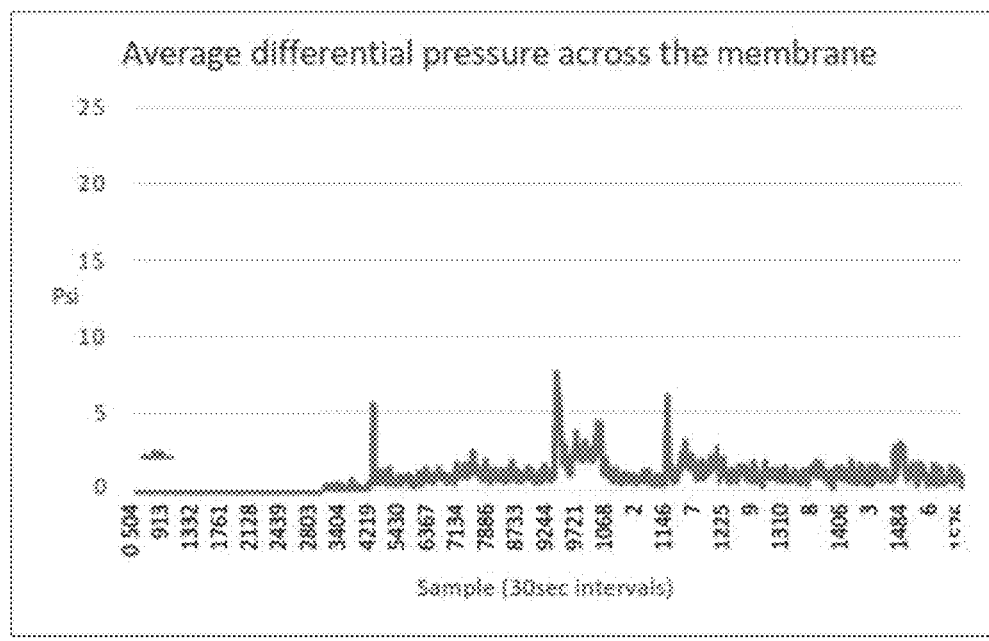
FIG. 8B is a graph showing the average pressure differential across a reverse osmosis membrane for the experiment of FIG. 8A.

Osmosis Membrane Control Example 1—The first experiment serves as a control that was inoculated with B. megaterium, but had no treatments on the membrane. The test was inoculated four times and the membrane was observed and samples taken at 0 hours, 48 hours, 96 hours, and 144 hours. During the experiment it was observed that biofilm accumulated at an increasing rate on the reverse osmosis membrane over time. The system flow rate remained at 1 gpm and the temperatures of the piston pump, chiller, and primary bulk tank did not fluctuate. Throughout the first control experiment the ΔP increased overall. FIGS. 8A and 8B show the ΔP across the membrane and average ΔP across the membrane for Osmosis Control Example 1.

Figure 9A:
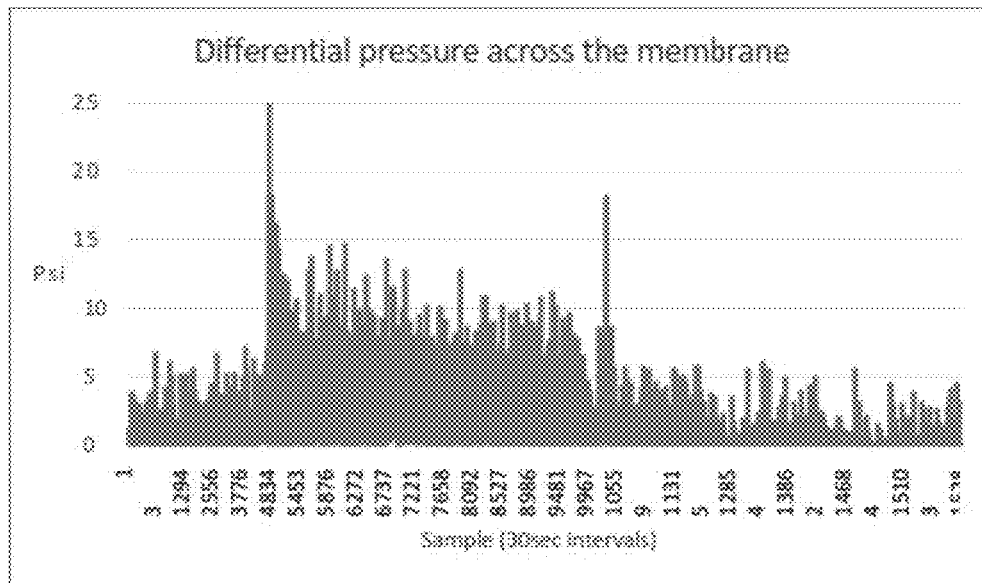
FIG. 9A is a graph showing raw data for the pressure differential across a reverse osmosis membrane during another experiment.
Figure 9B:
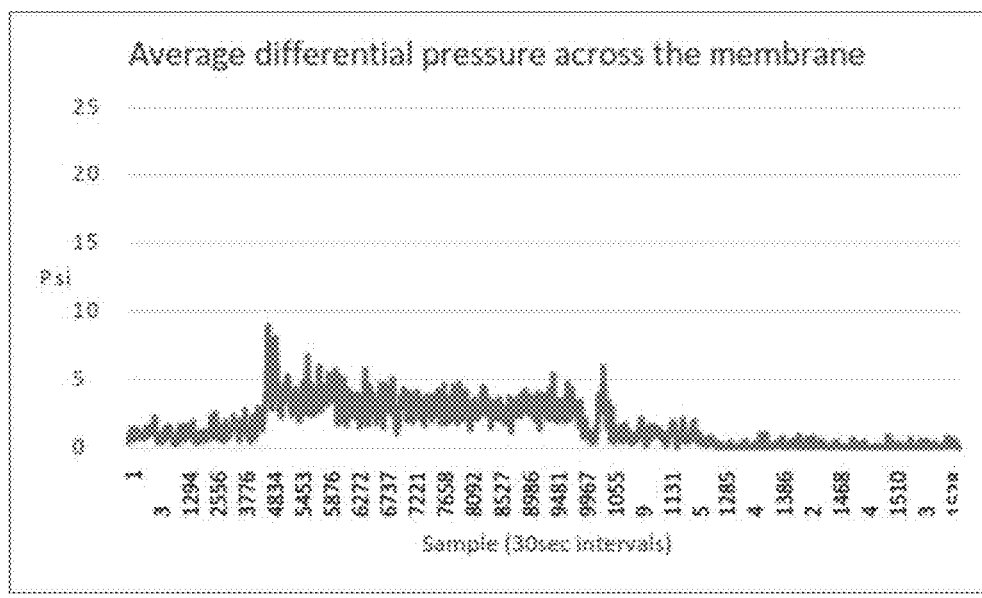
FIG. 9B is a graph showing the average pressure differential across a reverse osmosis membrane for the experiment of FIG. 9A.

Osmosis Membrane Control Example 2—The second control experiment was performed consistently to the first control experiment. Each experiment started with a new membrane. The primary bulk tank was inoculated every 48 hours with B. megaterium. The membrane was observed at 0 hours, 48 hours, 96 hours, and 144 hours. The membrane was not treated to observe the effect of biofouling on the membrane and the system components. The results of this control experiment showed that biofilm accumulation increased over time. The system's flow rate remained at 1 gpm with no fluctuation in temperatures for the bulk tank, pump, or chiller. The ΔP across the membrane did increase overall and had large pressure spikes from the pump. It was observed that the pressure spikes were frequent indicating a high ΔP throughout the experiment. Towards the end of the experiment the ΔP began to drop. This could have been a result of the piston pump reducing pressure swings due to the valves on the inlet or outlet opening or closing at different rates. The pump head then required maintenance on the outlet valves for the piston pump. The spring mechanisms on the valves became offset and were replaced. FIGS. 9A and 9B show the ΔP across the membrane and average ΔP across the membrane for Osmosis Control Example 2.

Osmosis Membrane Treatment Experiments—Three treatment experiments (nos. 3-6) were performed following the control experiments. The same parameters were maintained for each experiment. The feed pressure and the concentrate pressure were set to 300 psi. The system's flow rate was set to 1 gpm. B. megaterium was inoculated a total of four times each experiment, first at 0 hours, at 48 hours, at 96 hours, and at 144 hours. Before the inoculation of bacteria at 48, 96, and 144 hours, a treatment cycle varying between 2 to 5 hours and using a preferred treatment composition according to the invention was performed. The treatment composition used in the experiments comprises around 43.1% citric acid, around 5.2% Aerosol OS (surfactant), and around 52.2% sodium bicarbonate, all percentages by weight. Other treatment compositions according to the invention could also be used. The treatment composition was pre-mixed with water in a separate container before being transferred to the secondary loop tank (treatment feeder) 222 and pumped through the reverse osmosis cell in the secondary loop. The primary loop was offline while the secondary loop was online. To turn the primary loop back on, the back pressure regulator and the bypass were re-opened and adjusted back to operating parameters of the primary loop after each treatment cycle was complete. During treatment, permeate flux was not collected due to the lack of pressure applied to the reverse osmosis cell.

Figure 10A:
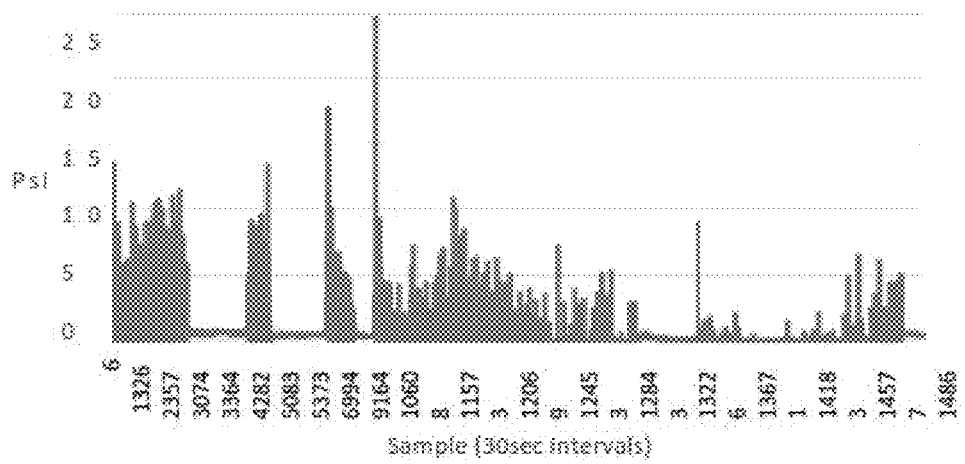
FIG. 10A is a graph showing raw data for the pressure differential across a reverse osmosis membrane during another experiment.
Figure 10B:
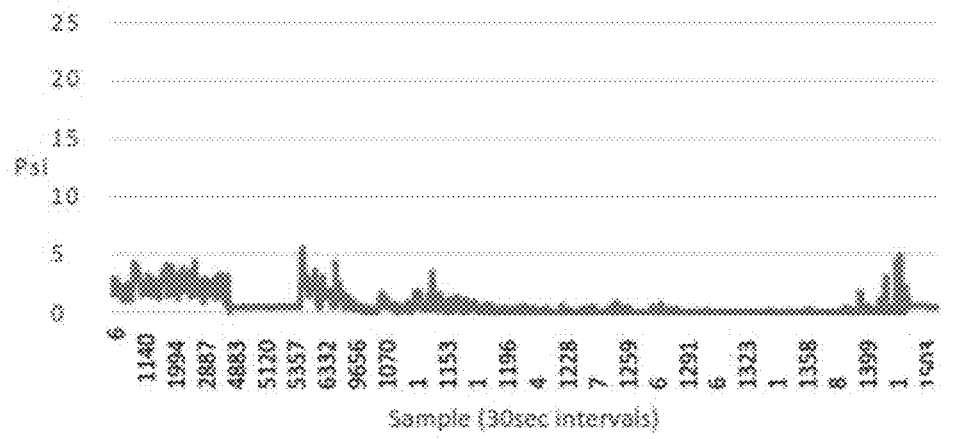
FIG. 10B is a graph showing the average pressure differential across a reverse osmosis membrane for the experiment of FIG. 10A.
Figure 11A:
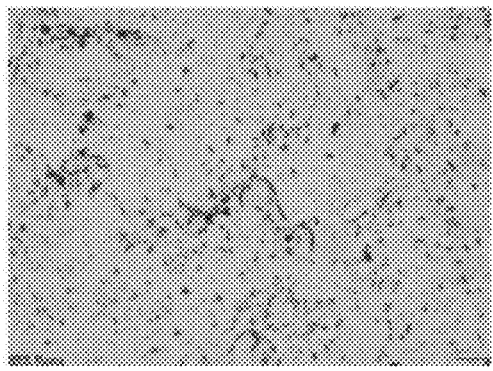
FIG. 11A are photographs of stains from samples taken prior to a treatment cycle showing bacteria concentration.
Figure 11A:
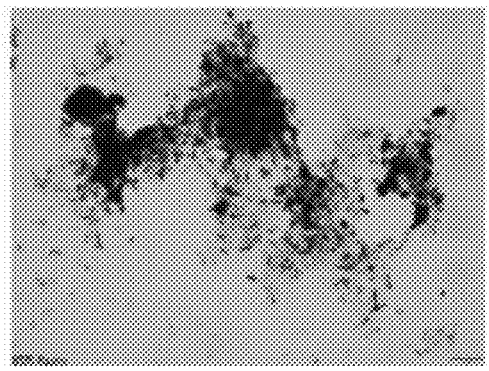
Figure 11A:
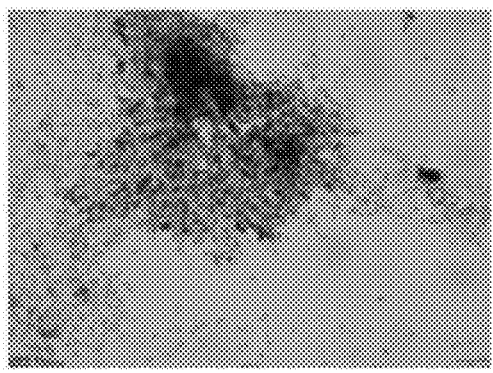
Figure 11A:
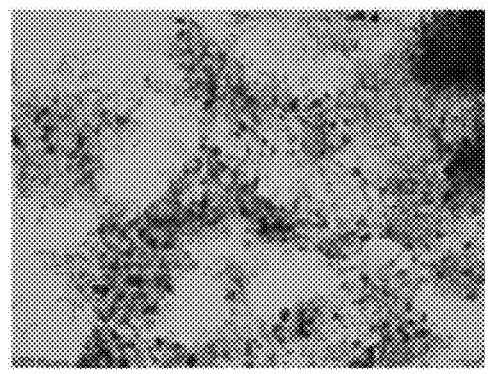
Figure 11B:
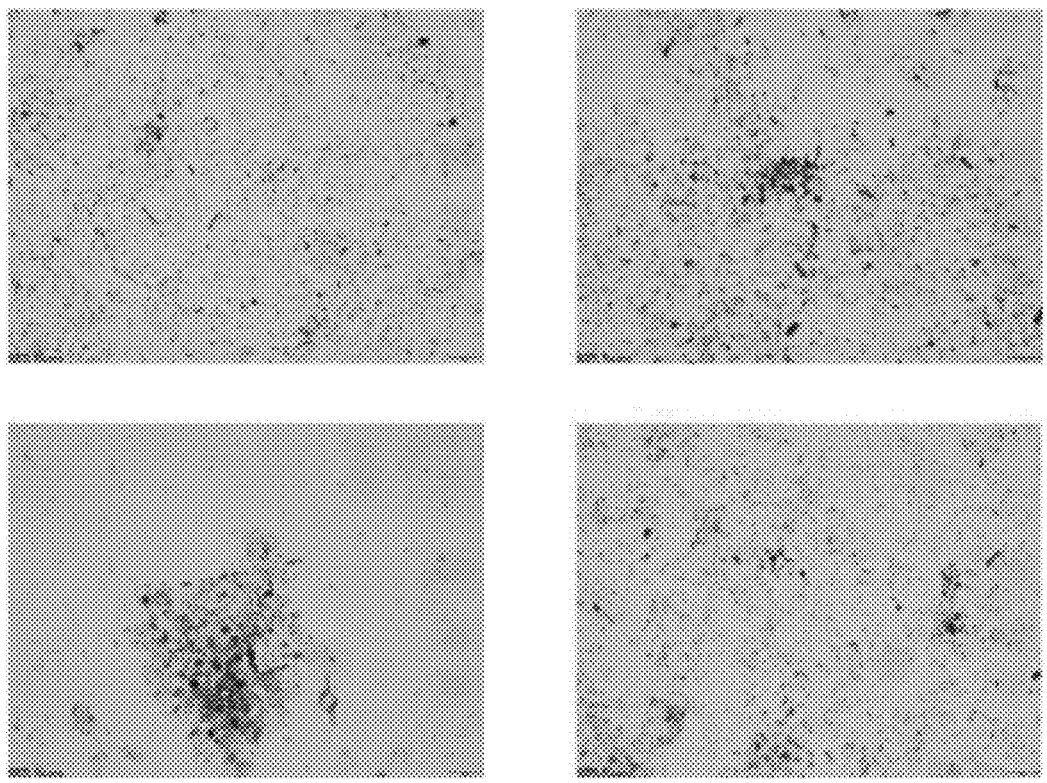
FIG. 11B are photographs of stains from samples taken after a treatment cycle showing bacteria concentration.

Osmosis Membrane Treatment Example 3—From the results of the first treatment test it was observed that biofilm was reduced after each treatment period. Each treatment period was 5 hours at a treatment composition concentration of 255 ppm in the volume of water flowing through the secondary loop (as that was the only loop in use for the experiments, in typical operation, the concentration of treatment composition would be at least 255 ppm in the total volume of water circulating through the reverse osmosis system). The 255 ppm concentration level was found to be the lowest effective concentration of treatment composition. Due to equipment errors, the back pressure regulator was not working properly. This resulted in the ΔP across the membrane to have more pressure swings from the piston pump and less control of the feed and concentrate pressure. The flow rate of the total system fluctuated between 0.5 gpm to 1.0 gpm. FIGS. 10A and 10B show the ΔP across the membrane and average ΔP across the membrane for Osmosis Treatment Example 3. The information from the graph shows that there was high pressure spikes randomly, and the graph showed a general decrease in slope over time, whereas the predicted trend with treatment was to see an increase or positive slope for the AP across the membrane since the primary system tank was inoculated with B. megaterium every 48 hours, thus increasing the concentration of biological presence in the system to foul the reverse osmosis membrane at a faster rate. This indicates the treatment was effective at removing biofilm buildup on the membrane, which reduced the pressure across the membrane during each treatment cycle. Even with each addition of B. megaterium, allowing the membrane to foul at an increased rate, the treatment composition was able to reduce the appearance of biofouling at each time interval. Swabs of the reverse osmosis membrane were taken randomly before and after each treatment cycle. These swab samples were analyzed by Gram stains to produce a qualitative analysis of population density of B. megaterium. FIGS. 11A and 11B show photographs of the stains before each treatment cycle (11A) and after each treatment cycle (11B). The dark spots show concentrations of or population density of B. megaterium. As can be seen, the amount of B. megaterium was reduced after treatment. Contamination from gram negative species present also decreased in population concentration.

Figure 12A:
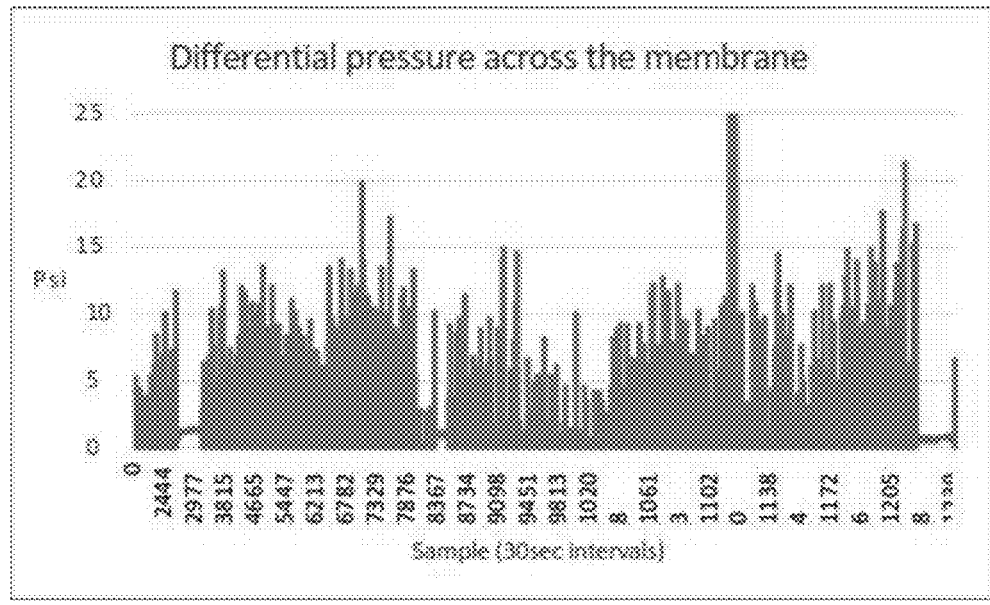
FIG. 12A is a graph showing raw data for the pressure differential across a reverse osmosis membrane during another experiment.
Figure 12B:
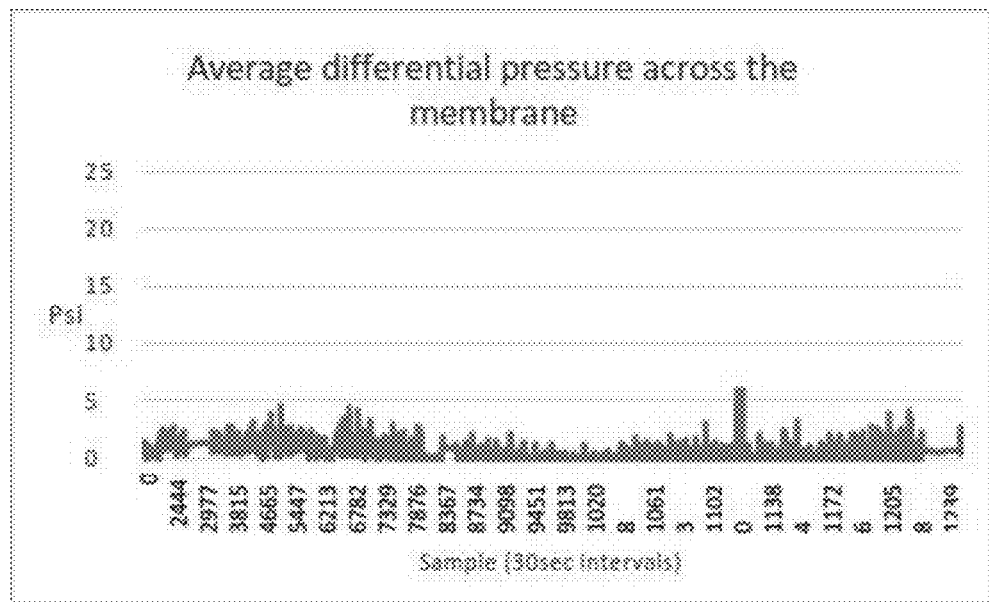
FIG. 12B is a graph showing the average pressure differential across a reverse osmosis membrane for the experiment of FIG. 12A.
Figure 13A:
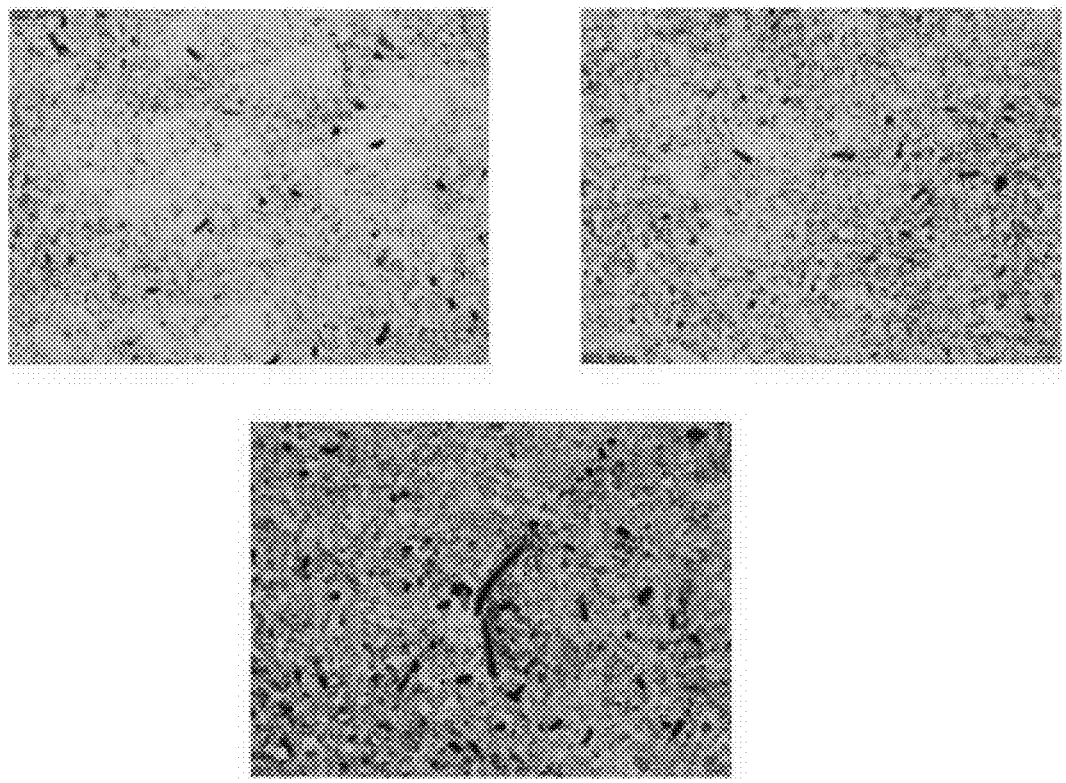
FIG. 13A are photographs of stains from samples taken prior to a treatment cycle showing bacteria concentration.
Figure 13B:
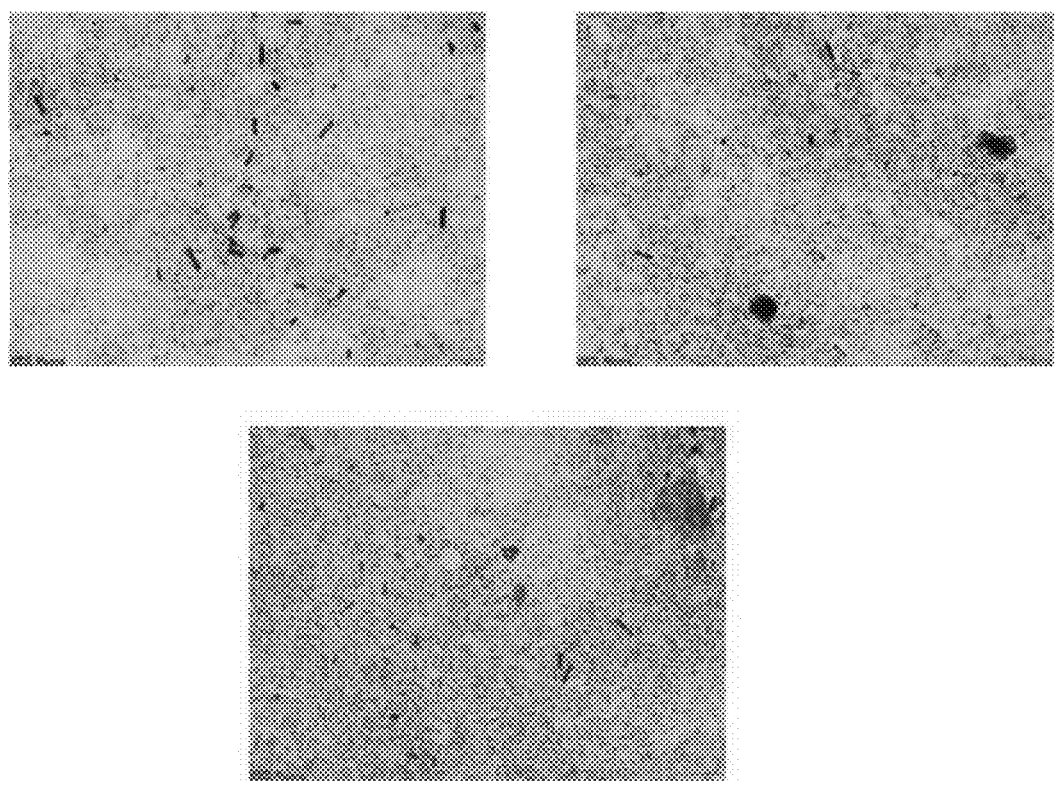
FIG. 13B are photographs of stains from samples taken after a treatment cycle showing bacteria concentration.

Osmosis Treatment Example 4—Example 4 had the same operating parameters previously stated for Osmosis Treatment Example 3 and all of the control runs (a new membrane was used for each experiment). The piston pump and all equipment were in operating condition, which reduced the amount pressure spikes for the ΔP and controlled the flow rate at 1 gpm without any fluctuation. While the secondary loop was online, the treatment cycle durations were decreased to see if treatment time was correlated to the efficacy of the treatment composition according to the preferred embodiment used in the experiments. The treatment cycles were reduced to 2 hours at a treatment composition concentration of 255 ppm in the volume of water flowing through the secondary loop. The results indicated that treatment cycle duration is important to the rate of removal of biofouling on the membrane. The trend for the ΔP had a positive slope over time, which was predicted to occur. FIGS. 12A and 12 B show the ΔP across the membrane and average ΔP across the membrane for Osmosis Treatment Example 4. Observation of the membrane showed that even with a decreased treatment cycle duration, biofilm was still removed. Comparing the results of Osmosis Treatment Experiments 3 and 4, which differed only in treatment cycle duration, at the lower end of treatment composition effective concentration (around 255 ppm), a longer treatment cycle is preferred to allow more time for the treatment composition to dissociate any biofouling present to fully clean the membrane (and by extension to fully clean other parts of the reverse osmosis system, if the treatment composition is circulated through the whole system). However, even a shorted treatment cycle curation of 2 hours at this low end concentration still removed some biofilm and had a positive impact on the reverse osmosis system. Swabs of the reverse osmosis membrane were taken randomly before and after each treatment cycle. These swab samples were analyzed by Gram stains to produce a qualitative analysis of population density of B. megaterium. FIGS. 13A and 13B show photographs of the stains before each treatment cycle (13A) and after each treatment cycle (13B). The dark spots show concentrations of or population density of B. megaterium. As can be seen, the amount of B. megaterium was reduced after treatment, but not as much as observed in Osmosis Treatment Example 3 with a longer treatment cycle duration.

Figures 14A, 14B:
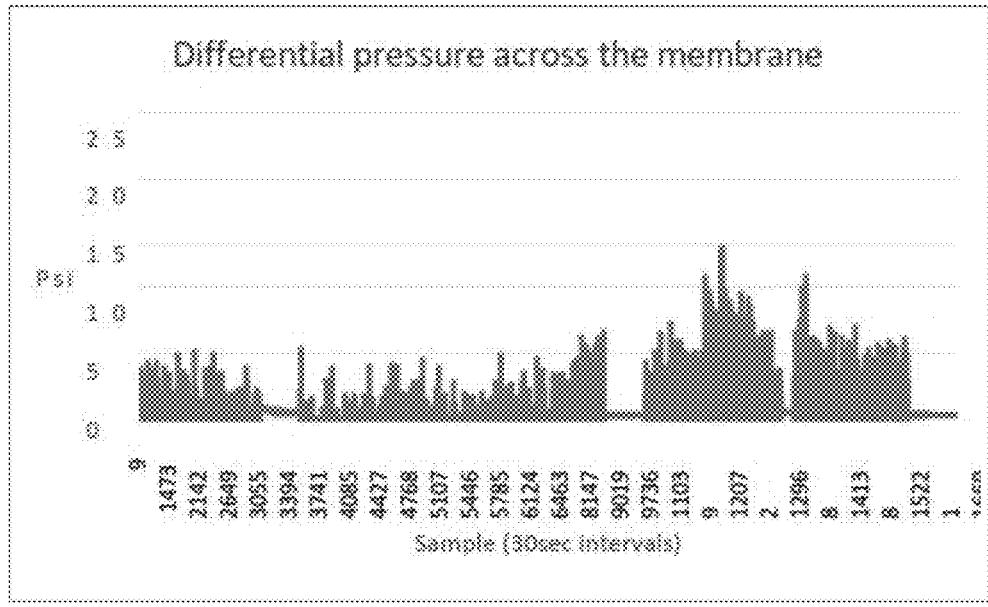
FIG. 14A is a graph showing raw data for the pressure differential across a reverse osmosis membrane during another experiment.
FIG. 14B is a graph showing the average pressure differential across a reverse osmosis membrane for the experiment of FIG. 14A.

Osmosis Treatment Example 5—This Example used the same operating parameters as the previous osmosis system experiments. When the secondary loop was online, the treatment cycle durations were again 5 hour intervals (like Osmosis Example 3). The treatment cycle was increased to 5 hours to further investigate the effect of exposure time on removal rate of biofilm for a treatment composition according to a preferred embodiment of the invention. A treatment composition concentration of 255 ppm in the volume of water flowing through the secondary loop was used. Maintenance was performed on the piston pump and the back pressure regulator to prevent any previously observed issues relating to the ΔP. The pressure spikes were again maintained and the flow rate of the total system was 1 gpm. No major issues were encountered in this example. The membrane was observed before and after each treatment cycle and indicated that the treatment composition was effective at removing biofouling from the membrane with low flow and low pressure. The ΔP was again a positive slope as previously predicted. FIGS. 14A and 14 B show the ΔP across the membrane and average ΔP across the membrane for Osmosis Treatment Example 5. With the 5 hour treatment cycles, it seemed that the pressure spikes for the piston pump were better maintained according to the differential graphs, along with decreasing the amount of noise the pump produced. The less stress the piston pump endured, the less energy usage was required to maintain the feed pressure, indicating that biofouling was controlled sufficiently to not decrease the permeate flux.

Figure 15:
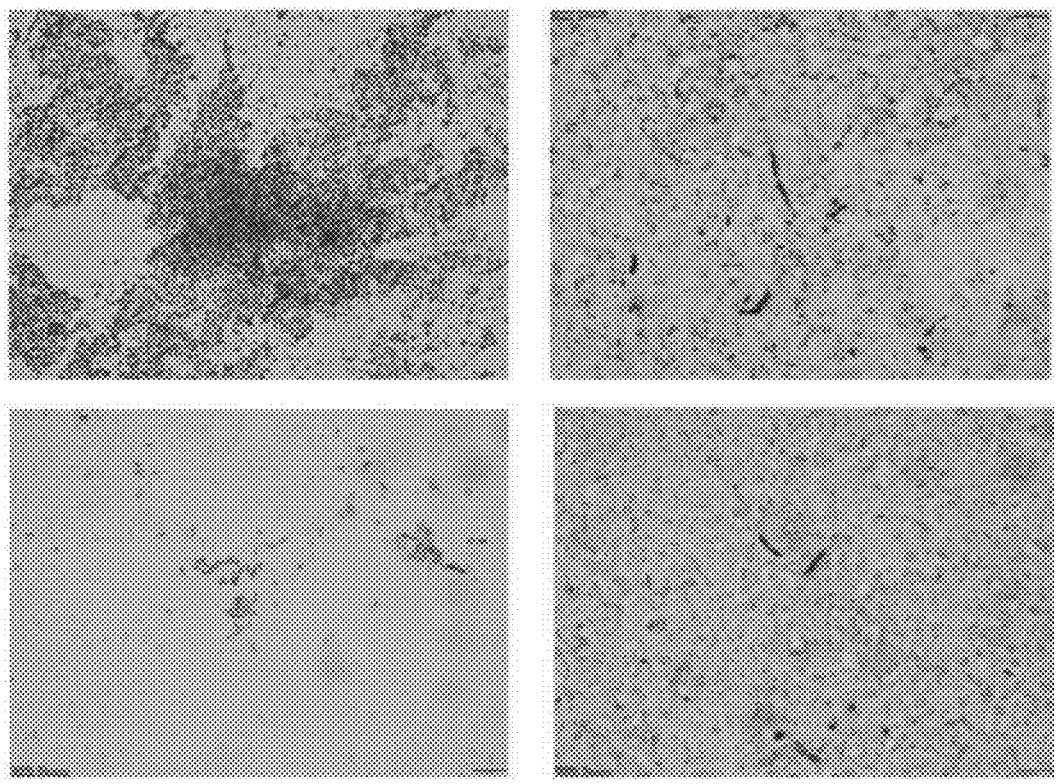
FIG. 15 show photographs of stains from samples taken before treatment (top two photos) and after treatment (bottom two photos).

Swabs of the reverse osmosis membrane were again taken randomly before and after each treatment cycle. These swab samples were analyzed by Gram stains to produce a qualitative analysis of population density of *B. megaterium*. FIG. 15 show photographs of the stains before treatment (top two photos) and after treatment (bottom two photos). The dark spots show concentrations of or population density of *B. megaterium*. As can be seen, the amount of *B. megaterium* was reduced after treatment. Serial dilutions were also run for Example 5. The $10^{-3}$ and $10^{-4}$ dilutions were chosen for quantification. Many of the before treatment plates were past the maximum detection point (300 cfl/ml). The after treatment plates were reduced significantly. The results are summarized in the table below.

TABLE 4

Serial Dilutions Before and After Treatment Cycles for Osmosis Treatment Example 5

| Treatment Cycle #/ Dilution | Bacteria Count Before Treatment | Bacteria Count After Treatment |
|---|---|---|
| 1 (just before 48 hrs)/ $10^{-3}$ | Over Max Detection Level | 0 cfu/ml (under minimum detection level |
| 1 (just before 48 hrs)/ $10^{-4}$ | $8.0^6$ cfu/ml | 0 cfu/ml (under minimum detection level |
| 2 (just before 96 hrs)/ $10^{-3}$ | Over Max Detection Level | $1.73^6$ cfu/ml |
| 2 (just before 96 hrs/ $10^{-4}$ | Over Max Detection Level | $4.5^6$ cfu/ml |
| 3 (just before 144 hrs)/ $10^{-3}$ | Over Max Detection Level | $7.0^4$ cfu/ml |
| 3 (just before 144 hrs)/ $10^{-4}$ | $1.64^7$ cfu/ml | $1.05^5$ cfu/ml |

The concentration of treatment composition in each example was measured according to the volume of the secondary loop, which was predetermined to be 4 liters. Table 5 shows the amount of active ingredients in the preferred treatment composition used in the example to achieve a concentration of 255 ppm in the 4 liter volume of water used for the experiments. The lowest concentration of the treatment composition was chosen to see how effective it was over time. With a lower concentration it is important to allow a longer treatment cycle time to remove any type of biofouling present. It was observed from each example conducted that 1 to 2 hour treatment cycle times at a low concentration were not as effective as 5 hour treatments. However, it was observed that the treatment composition was still able to remove biofilm even in a shorter treatment cycle at a lower concentration. Higher concentrations of treatment composition would require shorter treatment cycles.

A major issue with reverse osmosis membrane fouling is the restriction of permeate flux output. An increase of a biological presence on the membrane results in reduced permeate flux and possible membrane degradation. The permeate flux was compared between control experiments and treatment experiments (with permeate collected during non-treatment cycles). Osmosis Control Example 2 permeate was compared to Osmosis Treatment Example 5 permeate. Only the total mass was recorded for the permeate flux. Each example started with a new permeate collection tank 144 that weighed 1.23 kg. Table 5 below shows the permeate collection data from these experiments.

TABLE 5

Permeate Collection in Osmosis Experiments 2 and 5

| | Time (hrs) | Total Mass (kg) |
|---|---|---|
| RO Permeate Flux Example 2 (no treatment) | 166.5 | 13.58 |
| RO Permeate Flux Example 5 (with treatment) | 166.5 | 19.03 |

All experiments were run for 166.5 hours of permeate collection time (the total experiment time for treatment experiments was longer to account for each of the treatment cycles). The total mass recorded from Osmosis Control Example 2 13.58 kg. The total mass recorded from Osmosis Treatment Example 5 was 19.03 kg, increasing the permeate flux by 5.45 kg or around 40%. These results indicate that treatment with treatment compositions and methods according to the invention are effective at preventing a decrease in permeate flux for the reverse osmosis membrane system that normally occurs as a result of biofouling.

Osmosis Treatment Example 6—Another experiment was conducted to test the efficacy of a preferred treatment composition according to the invention on the entire reverse osmosis membrane system coupled with a secondary biocide treatment. The primary loop treatment was treated over a 24 hour duration after the membrane and entire reverse osmosis, system were completely fouled by *B. megaterium*. It was determined that the volume of water in the reverse osmosis system used in the experiment (the primary loop) was around 19 liters. Sufficient treatment composition was added to provide a concentration of 255 ppm in the 19 liters of water volume in the reverse osmosis system. The treatment composition was added as a single dose at the beginning of the 24 hour treatment cycle. A secondary biocide, 500 ml of hypochlorite, was added after the treatment composition was added immediately after adding the treatment composition, resulting in a concentration of 9,000 ppm based on 19 liters of water in the reverse osmosis system. Both the treatment composition and hypochlorite were added directly into primary bulk tank 112 for purposes of this example. Most preferably, in an actual reverse osmosis system, treatment composition would be fed through a feeder 222 connected to a side loop (the secondary loop) or tied into one of the process lines for the reverse osmosis system. Any separate treatments, such as a separately added secondary biocide, may be added through the same feeder 222 or through another tank or port in the treatment system or reverse osmosis system. An additional bag filter (1 micron pore size) was installed at the end of the concentrate line 152 returning back to the primary bulk tank 112 to collect any debris removed. No parameters such as the ΔP, Pf, $P_c$, primary bulk tank temperature, chiller temperature, pump motor temperature, or flow rate were recorded and no microbial data was collected for this example, rather the results of the experiment were based on visual inspect of the membrane and components of the reverse osmosis system before and after treatment. The membrane and inlet and outlet tubing of the chiller were visually inspected at 0 hours (just before addition of the treatment composition, but after the reverse osmosis system had been inoculated with bacteria and fully fouled), 5 hours, 20 hours, and 24 hours. These components all showed significant biofilm at the beginning of the experiment, but after 24 hours of treatment, the biofilm was substantially reduced and virtually eliminated. This indicates that a longer treatment cycle of around 24 hours at a low concentration of treatment composition, particularly coupled with an optional secondary biocide, is very effective at removing biofilm in a reverse osmosis system.

The concentration ranges for the active ingredients (such as an acid, salt, and surfactant) of treatment compositions provided herein are based on the quantities of these reagents in the total volume of water in the water system being treated, prior to the addition of any other additives, such as corrosion inhibitors, anti-foaming agents, or any secondary biocide. Such additives may be incorporated into a pre-mixed treatment composition according to an embodiment of the invention and those of ordinary skill in the art will understand and appreciate the corresponding change in concentrations when the additional ingredients are included. References herein to water systems that are not capable of holding a volume of water include systems that are actually capable of holding a volume of water, either as they currently exist or through modification, but for which it is desired for any reason to apply the treatment composition of the invention without plugging the system or otherwise using an shut-off mechanism to hold a volume of water within the system. Additionally, the use of the terms flowing (or circulating) and non-flowing (or non-circulating) to describe water systems is not intended to limit the scope of the invention, as the embodiments of the composition, method, and system may be used with either type of system with modifications described herein or that will be understood by those of ordinary skill in the art. With respect to use in connection with reverse osmosis and other membrane systems, the reverse osmosis system described herein is a water system, but other solvents (or other fluids) may be used with reverse osmosis and other membrane systems treated according to the invention and the concentrations of active ingredients would be with respect to the total volume of the solvent (or other fluid) in the osmosis or other membrane system. Those of ordinary skill in the art will also appreciate upon reading this specification, including the examples contained herein, that modifications and alterations to the composition and methodology and system for using the composition may be made within the scope of the invention and it is intended that the scope of the invention disclosed herein be limited only by the broadest interpretation of the appended claims to which the inventor is legally entitled.

We claim:

1. A method of removing biofilm and treating a fluid system containing a membrane, the method comprising the steps of:
    adding a surfactant, a first chelating agent, and a second chelating agent or other ingredient that will react with the first chelating agent to produce a second chelating agent to the fluid system in amounts sufficient to provide concentrations of at least 0.00015 M for the surfactant, about 0.001M to 0.01M for the first chelating agent, and about 0.0005 M to 0.005M for the second chelating agent when mixed with a volume of fluid in the fluid system containing the membrane or portion thereof being treated;
    removing biofilm by circulating the fluid containing the surfactant and chelating agents through at least a portion of the fluid system to contact the membrane;
    wherein the membrane is a nanofiltration, ultrafiltration, microfiltration, forward osmosis, reverse osmosis, or particle filtration membrane;
    wherein the fluid system is a water system and the fluid comprises water; and
    wherein the first chelating agent is citric acid, the second chelating agent is sodium citrate, and the other ingredient is sodium bicarbonate.

2. The method of claim 1 further comprising the steps of:
    adding a corrosion inhibitor and a biocide to the fluid in the fluid system; and
    circulating the fluid containing the corrosion inhibitor and the biocide through at least a portion of the fluid system.

3. The method according to claim 1 wherein the surfactant is an ammonium bromide compound, an ammonium chloride compound, or a sodium sulfonate compound.

4. The method of claim 1 wherein the fluid system is a reverse osmosis system comprising the membrane, a feed line for feeding the fluid to the membrane, a concentrate line exiting the membrane and a permeate line exiting the membrane, the method further comprising the step of:
    flowing the fluid containing the surfactant and chelating agents from the feed line to the concentrate line to contact the membrane.

5. The method of claim 2 wherein the corrosion inhibitor is added and circulated for a period of time prior to adding the surfactant.

6. The method of claim 2 wherein the surfactant is added and circulated for a period of time prior to adding the first chelating agent.

7. The method of claim 2 wherein the surfactant and chelating agents circulate for a period of time prior to adding the biocide.

8. The method of claim 2 wherein the surfactant, the first chelating agent, the second chelating agent or other ingredient that will react with the first chelating agent to produce a second chelating agent, and biocide are added at the same time.

9. The method of claim 4 further comprising the step of removing substantially all of the fluid containing the surfactant and chelating agents from the reverse osmosis system after the circulating step; and
    rinsing the reverse osmosis system.

10. The method according to claim 4 wherein the surfactant is in a range of about 0.00015 M to 0.0015 M when mixed with the volume of fluid in the reverse osmosis system being treated.

11. The method of claim 4 further comprising the step of filtering the fluid as it circulates through the reverse osmosis system to remove dislodged biofilm material.

12. The method according to claim 4 wherein the surfactant, the first chelating agent, and the second chelating agent or other ingredient that will react with the first chelating agent to produce a second chelating agent are in solid form prior to being added to the fluid of the reverse osmosis system being treated.

13. The method of claim 4 wherein the adding step comprises diverting at least some fluid from the concentrate line to a treatment system comprising a feeder containing the surfactant and chelating agents in dry or powdered form and adding the surfactant and chelating agents to the diverted fluid.

14. The method of claim 13 wherein the circulating step further comprises returning the diverted fluid with the surfactant and chelating agents to the feed line to flow from the feed line to the concentrate line to contact the membrane.

* * * * *